United States Patent
Franke et al.

(10) Patent No.: US 10,201,709 B2
(45) Date of Patent: Feb. 12, 2019

(54) DEPLETION BLOCK TO BLOCK NERVE COMMUNICATION

(71) Applicant: Cardiac Pacemakers, Inc., St. Paul, MN (US)

(72) Inventors: Manfred Franke, Weissenborn Sa. (DE); David J. Ternes, Roseville, MN (US); Juan Gabriel Hincapie Ordonez, Maple Grove, MN (US); Stephen B. Ruble, Lino Lakes, MN (US); Jason J. Hamann, Blaine, MN (US); Arjun D. Sharma, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 593 days.

(21) Appl. No.: 14/597,137

(22) Filed: Jan. 14, 2015

(65) Prior Publication Data

US 2015/0202441 A1    Jul. 23, 2015

Related U.S. Application Data

(60) Provisional application No. 61/928,725, filed on Jan. 17, 2014.

(51) Int. Cl.
*A61B 18/12* (2006.01)
*A61N 1/36* (2006.01)
(Continued)

(52) U.S. Cl.
CPC ........ *A61N 1/3611* (2013.01); *A61B 18/1206* (2013.01); *A61N 1/0551* (2013.01);
(Continued)

(58) Field of Classification Search
CPC ... A61B 18/1206; A61B 18/082; A61B 18/12; A61B 18/14; A61B 18/1402;
(Continued)

(56) References Cited

U.S. PATENT DOCUMENTS

| 4,608,985 A | 9/1986 | Crish et al. |
| 5,421,817 A | 6/1995 | Liss et al. |

(Continued)

FOREIGN PATENT DOCUMENTS

| AU | 2015206540 B2 | 8/2017 |
| AU | 2015206541 B2 | 12/2017 |

(Continued)

OTHER PUBLICATIONS

Bhakta, Bipin B, et al., "Management of spasticity in stroke", British Medical Bulletin, 56 (No. 2), (2000), 476-485.

(Continued)

*Primary Examiner* — Thomas Giuliani
(74) *Attorney, Agent, or Firm* — Schwegman Lundberg & Woessner, P.A.

(57) ABSTRACT

An example of a system may include a depletion block neural stimulator and a depletion block controller. The depletion block neural stimulator may be configured to deliver a depletion block stimulation to a nerve. The depletion block stimulation may include a series of pulses at a pulse frequency within a range between about 100 Hz to about 1000 Hz. The depletion block controller may be configured to communicate with the depletion block neural stimulator and control the depletion block stimulation. The depletion block controller may be configured to receive a start depletion block signal and respond to the received start depletion block signal by initiating the delivery of the depletion block stimulation to the nerve, and the depletion block controller may be configured to receive a stop deple- (Continued)

tion block signal and respond to the received stop depletion block signal by terminating the delivery of the depletion block stimulation to the nerve.

8 Claims, 10 Drawing Sheets

(51) Int. Cl.
*A61N 1/05* (2006.01)
*A61B 18/00* (2006.01)
*A61N 1/372* (2006.01)
*A61N 1/378* (2006.01)
*A61B 18/14* (2006.01)
*A61B 18/20* (2006.01)

(52) U.S. Cl.
CPC ....... *A61N 1/0558* (2013.01); *A61N 1/36053* (2013.01); *A61N 1/36067* (2013.01); *A61N 1/36071* (2013.01); *A61N 1/36117* (2013.01); *A61N 1/36128* (2013.01); *A61N 1/36171* (2013.01); *A61B 18/1477* (2013.01); *A61B 18/20* (2013.01); *A61B 2018/00577* (2013.01); *A61B 2018/00595* (2013.01); *A61N 1/36132* (2013.01); *A61N 1/36135* (2013.01); *A61N 1/3787* (2013.01); *A61N 1/37205* (2013.01); *A61N 1/37288* (2013.01)

(58) Field of Classification Search
CPC ........... A61B 2018/00577; A61B 2018/00434; A61B 2018/0044; A61B 2018/128; A61N 2001/34; A61N 1/36071; A61N 1/0551; A61N 1/36067; A61N 1/36128; A61N 1/36132; A61N 1/06
USPC .................................. 606/33, 34, 41; 607/46
See application file for complete search history.

(56) References Cited

U.S. PATENT DOCUMENTS

| | | | |
|---|---|---|---|
| 7,389,145 | B2 | 6/2008 | Kilgore et al. |
| 7,734,355 | B2 | 6/2010 | Cohen et al. |
| 7,826,899 | B1 | 11/2010 | Ryu et al. |
| 7,949,399 | B2 | 5/2011 | Wenzel et al. |
| 8,060,208 | B2 | 11/2011 | Kilgore et al. |
| 8,229,564 | B2 | 7/2012 | Rezai et al. |
| 8,483,831 | B1 | 7/2013 | Hlavka et al. |
| 9,242,097 | B2 | 1/2016 | Mokelke et al. |
| 2002/0055779 | A1 | 5/2002 | Andrews |
| 2003/0233137 | A1 | 12/2003 | Paul, Jr. |
| 2004/0093093 | A1 | 5/2004 | Andrews |
| 2004/0127953 | A1 | 7/2004 | Kilgore et al. |
| 2005/0021092 | A1 | 1/2005 | Yun et al. |
| 2005/0137644 | A1 | 6/2005 | Boveja et al. |
| 2005/0149148 | A1* | 7/2005 | King .................. A61N 1/36007 607/70 |
| 2005/0216070 | A1 | 9/2005 | Boveja et al. |
| 2006/0200208 | A1 | 9/2006 | Terry, Jr. et al. |
| 2006/0253161 | A1 | 11/2006 | Libbus et al. |
| 2007/0027496 | A1 | 2/2007 | Parnis et al. |
| 2007/0073356 | A1 | 3/2007 | Rooney et al. |
| 2007/0191902 | A1 | 8/2007 | Errico et al. |
| 2007/0213771 | A1 | 9/2007 | Spinner et al. |
| 2008/0183248 | A1 | 7/2008 | Rezai et al. |
| 2008/0208305 | A1 | 8/2008 | Rezai et al. |
| 2009/0204173 | A1 | 8/2009 | Fang et al. |
| 2009/0281593 | A9 | 11/2009 | Errico et al. |
| 2010/0023088 | A1 | 1/2010 | Stack et al. |
| 2010/0070004 | A1 | 3/2010 | Hlavka et al. |
| 2010/0094376 | A1 | 4/2010 | Penner et al. |
| 2010/0114261 | A1 | 5/2010 | Errico et al. |
| 2010/0191311 | A1* | 7/2010 | Scheiner .............. A61N 1/0556 607/62 |
| 2010/0217347 | A1 | 8/2010 | Swoyer et al. |
| 2010/0228310 | A1 | 9/2010 | Shuros et al. |
| 2010/0241190 | A1 | 9/2010 | Kilgore et al. |
| 2010/0324630 | A1 | 12/2010 | Lee et al. |
| 2011/0009927 | A1* | 1/2011 | Parker ................. A61N 1/0551 607/62 |
| 2011/0118725 | A1 | 5/2011 | Mayse et al. |
| 2011/0125216 | A1 | 5/2011 | Kilgore et al. |
| 2011/0184486 | A1 | 7/2011 | De Ridder |
| 2012/0059437 | A1 | 3/2012 | Shalev |
| 2012/0172680 | A1 | 7/2012 | Gelfand et al. |
| 2012/0221087 | A1 | 8/2012 | Parnis et al. |
| 2013/0138193 | A1 | 5/2013 | Durand et al. |
| 2013/0289678 | A1 | 10/2013 | Clark et al. |
| 2014/0018788 | A1 | 1/2014 | Engelman et al. |
| 2014/0364921 | A1 | 12/2014 | Legay et al. |
| 2014/0364923 | A1 | 12/2014 | Legay et al. |
| 2015/0202437 | A1 | 7/2015 | Franke et al. |
| 2015/0202444 | A1 | 7/2015 | Franke et al. |
| 2015/0202446 | A1 | 7/2015 | Franke et al. |

FOREIGN PATENT DOCUMENTS

| | | |
|---|---|---|
| CN | 106573139 A | 4/2017 |
| CN | 106573143 A | 4/2017 |
| CN | 106573144 A | 4/2017 |
| CN | 106573145 A | 4/2017 |
| EP | 3094369 B1 | 1/2018 |
| JP | 2006508768 A | 3/2006 |
| JP | 2011502022 A | 1/2011 |
| JP | 2011502586 A | 1/2011 |
| JP | 2017502786 A | 1/2017 |
| JP | 2017502787 A | 1/2017 |
| KR | 20120126140 A | 11/2012 |
| KR | 1020120126140 A | 11/2012 |
| WO | WO-2007103324 A1 | 9/2007 |
| WO | WO-2009058258 A1 | 5/2009 |
| WO | WO-2010019481 A1 | 2/2010 |
| WO | WO-2012021583 A1 | 2/2012 |
| WO | WO-2013018083 A2 | 2/2013 |
| WO | WO-2015109015 A1 | 7/2015 |
| WO | WO-2015109018 A1 | 7/2015 |
| WO | WO-2015109023 A1 | 7/2015 |
| WO | WO-2015109024 A1 | 7/2015 |

OTHER PUBLICATIONS

Canning, Brendan J., et al., "Evidence That Distinct Neural Pathways Mediate Parasympathetic Contractions and Relaxations of Guinea-Pig Trachealis", Journal of Physiology (1993), 471, (1993), 25-40.

Canning, Brendan J., "Reflex regulation of airway smooth muscle tone", J Appl Physiol 101, (2006), 971-985.

Chang, C. C., et al., "Mechanisms of the inhibition by neostigmine of tetanic contraction in the mouse diaphragm", Br. J. Pharmac. 87, (1986), 757-762.

Coleridge, H M, et al., "Characteristics of C Fibre Baroreceptors in the Carotid Sinus of Dogs", J. Physiol. (1987), 394, (1987), 291-313.

Franke, Manfred, et al., "Depletion Block to Block Nerve Communication", U.S. Appl. No. 61/928,725, filed Jan. 17, 2014.

Franke, Manfred, et al., "Selective Nerve Stimulation Using Presynaptic Terminal Depletion Block", U.S. Appl. No. 61/928,732, filed Jan. 17, 2014.

Franke, Manfred, et al., "Systems and Methods for Delivering Pulmonary Therapy", U.S. Appl. No. 61/928,714, filed Jan. 17, 2014.

Franke, Manfred, et al., "Systems and Methods for Selective Stimulation of Nerve Fibers in Carotid Sinus", U.S. Appl. No. 61/928,707, filed Jan. 17, 2014.

Gosens, Reinould, et al., "Muscarinic receptor signaling in the pathophysiology of asthma and COPD", Respiratory Research 2006, 7:73, (2006), 1-15.

(56) References Cited

OTHER PUBLICATIONS

Hoffman, Thomas J., et al., "Inhibition of Histamine-Induced Bronchoconstriction in Guinea Pig and Swine by Pulsed Electrical Vagus Nerve Stimulation", Neuromodulation vol. 12; No. 4, (2009), 261-269.
Hoffman, Thomas J., et al., "Low Voltage Vagal Nerve Stimulation Reduces Bronchoconstriction in Guinea Pigs Through Catecholamine Release", Neuromodulation. 2012 ; 15(6), (2012), 527-536.
Kilgore, Kevin, et al., "Combined Direct Current and High Frequency Nerve Block for Elimination of the Onset Response", 31st Annual International Conference of the IEEE EMBS, Minneapolis, Minnesota, USA, Sep. 2-6, 2009, (2009), 197-199.
Kilgore, Kevin L, et al., "Reversible Nerve Conduction Block Using Kilohertz Frequency Alternating Current", Neuromodulation: Technology at the Neural Interface, (2013), 13 pgs.
Krzyzaniak, Michael J., et al., "Efferent vagal nerve stimulation attenuates acute lung injury following burn: The importance of the gut-lung axis", Surgery; 150(3):, (Sep. 2011), 379-389.
Lopez, Nicole E, et al., "Vagal Nerve Stimulation Blocks Peritoneal Macrophage Inflammatory Responsiveness after Severe Burn Injury", Shock. Aug. 2012 ; 38(3):, (Aug. 2012), 294-300.
Mokelke, Eric A., et al., "System and Method for Mapping Baroreceptors", U.S. Appl. No. 61/836,431, filed Jun. 18, 2013.
Paton, Julian, et al., "The Carotid Body as a Therapeutic Target for the Treatment of Sympathetically Mediated Diseases", Hypertension. 2013; 61, (2013), 5-13.
Seagard, J L, et al., "Firing characteristics of single-fiber carotid sinus baroreceptors.", Circulation Research Journal of The American Heart Association; 66:1499-1509, (1990), 12 pgs.
Sepulveda, P., et al., "Treatment of asthmatic bronchoconstriction by percutaneous low voltage nerve stimulation: case report", The Internet Journal of Asthma, Allergy and Immunology, vol. 7 No. 2, (2008).
Solomonow, M., et al., "Control of Muscle Contractile Force Through Indirect High-Frequency Stimulation", Amer. Journal of Physical Med.; vol. 62 No. 2, (1983), 71-82.
Strickland, Michael, et al., "Carotid Chemoreceptor Modulation of Regional Blood Flow Distribution During Exercise in Health and Chronic Heart Failure", Circulation Research. 100., (2007), 1371-1378.
Tkacova, Ruzena, "Systemic Inflammation in Chronic Obstructive Pulmonary Disease:May Adipose Tissue Play a Role? Review of the Literature and Future Perspectives", Mediators of Inflammation; vol. 2010, Article ID 585989, (2010), 1-12.
Undem, Bradley J., et al., "Autonomic Neural Control of Intrathoracic Airways", American Physiological Society; Comprehensive Physiology; 2, (2012), 1241-1267.
Undem, Bradley J., et al., "The Role of Vagal Afferent Nerves in Chronic Obstructive Pulmonary Disease", Proceedings of the American Thoracic Society vol. 2, (2005), 355-360.
Van Den Berge, M., et al., "Clinical and inflammatory determinants of bronchial hyperresponsiveness in COPD", Eur Respir J; 40:, (2012), 1098-1105.
Wine, Jeffrey J., et al., "Parasympathetic control of airway submucosal glands: Central reflexes and the airway intrinsic nervous system", Autonomic Neuroscience: Basic and Clinical 133, (2007), 35-54.
Wodlinger, Brian, et al., "Block of Peripheral Pain Response by High-Frequency Sinusoidal Stimulation", Neuromodulation; 16, (2013), 312-317.
Zhang, Yong, et al., "Ganglionated Plexi Ablation for Atrial Fibrillation", Basic Research and Clinical Applications, Prof. Jong-Il Choi (Ed.), ISBN: 978-953-307-399-6, InTech,, Available from: http://www.intechopen.com/books/atrial-fibrillation-basic-research-andclinical-applications/ganglionated-plexi-ablation-for-atrial-fibrillation, (2012), 239-255.
"U.S. Appl. No. 14/597,112, Final Office Action dated Jul. 12, 2017", 10 pgs.
"U.S. Appl. No. 14/597,112, Non Final Office Action dated Jan. 13, 2017", 10 pgs.
"U.S. Appl. No. 14/597,112, Response filed Apr. 13, 2017 to Non Final Office Action dated Jan. 13, 2017", 9 pgs.
"U.S. Appl. No. 14/597,131, Advisory Action dated Nov. 4, 2016", 5 pgs.
"U.S. Appl. No. 14/597,131, Final Office Action dated Jul. 28, 2016", 14 pgs.
"U.S. Appl. No. 14/597,131, Final Office Action dated Aug. 23, 2017", 18 pgs.
"U.S. Appl. No. 14/597,131, Non Final Office Action dated Feb. 24, 2017", 16 pgs.
"U.S. Appl. No. 14/597,131, Non Final Office Action dated Mar. 28, 2016", 16 pgs.
"U.S. Appl. No. 14/597,131, Response filed May 18, 2017 to Non Final Office Action dated Feb. 24, 2017", 24 pgs.
"U.S. Appl. No. 14/597,131, Response filed Sep. 28, 2016 to Final Office Action dated Jul. 28, 2016", 12 pgs.
"U.S. Appl. No. 14/597,131, Response filed Dec. 28, 2016 to Final Office Action dated Jul. 28, 2016", 12 pgs.
"U.S. Appl. No. 14/597,145, Final Office Action dated Nov. 10, 2016", 14 pgs.
"U.S. Appl. No. 14/597,145, Non Final Office Action dated Mar. 1, 2017", 14 pgs.
"U.S. Appl. No. 14/597,145, Non Final Office Action dated May 16, 2016", 11 pgs.
"U.S. Appl. No. 14/597,145, Response filed Feb. 10, 2017 to Final Office Action dated Nov. 10, 2016", 9 pgs.
"U.S. Appl. No. 14/597,145, Response filed Jun. 1, 2017 to Non Final Office Action dated Mar. 1, 2017", 11 pgs.
"U.S. Appl. No. 14/597,145, Response filed Aug. 16, 2016 to Non Final Office Action dated Jun. 16, 2016", 10 pgs.
"U.S. Appl. No. 14/597,131, Response filed Jun. 28, 2016 to Non Final Office Action dated Mar. 28, 2016", 15 pgs.
"Australian Application Serial No. 2015206540, Office Action dated Nov. 7, 2016", 3 pgs.
"Australian Application Serial No. 2015206540, Response filed Apr. 6, 2017 to Office Action dated Nov. 7, 2016", 12 pgs.
"Australian Application Serial No. 2015206541, First Examiners Report dated Oct. 11, 2016", 3 pgs.
"Australian Application Serial No. 2015206541, Response filed Jul. 27, 2017 to First Examiners Report dated Oct. 11, 2016", 15 pgs.
"European Application Serial No. 15701907.6, Response filed Mar. 24, 2017 to Communication Pursuant to Rules 161(1) and 162 EPC dated Sep. 22, 2016", 7 pgs.
"European Application Serial No. 15701908.4, Response filed Apr. 10, 2017 to Communication Pursuant to Rules 161(1) and 162 EPC dated Sep. 30, 2016", 7 pgs.
"European Application Serial No. 15701910.0, Response filed Apr. 3, 2017 to Communication Pursuant to Rules 161(1) and 162 EPC dated Oct. 5, 2016", 14 pgs.
"European Application Serial No. 15702608.9, Response filed Mar. 29, 2017 to Communication Pursuant to Rules 161(1) and 162 EPC dated Sep. 21, 2016", 9 pgs.
"International Application Serial No. PCT/US2015/011458, International Preliminary Report on Patentability dated Jul. 28, 2016", 7 pgs.
"International Application Serial No. PCT/US2015/011458, International Search Report dated Mar. 31, 2015", 3 pgs.
"International Application Serial No. PCT/US2015/011458, Written Opinion dated Mar. 31, 2015", 5 pgs.
"International Application Serial No. PCT/US2015/011461, International Preliminary Report on Patentability dated Jul. 28, 2016", 8 pgs.
"International Application Serial No. PCT/US2015/011461, International Search Report dated Mar. 27, 2015", 6 pgs.
"International Application Serial No. PCT/US2015/011461, Written Opinion dated Mar. 27, 2015", 7 pgs.
"International Application Serial No. PCT/US2015/011467, International Preliminary Report on Patentability dated Jul. 28, 2016", 10 pgs.
"International Application Serial No. PCT/US2015/011467, International Search Report dated Mar. 26, 2015", 5 pgs.
"International Application Serial No. PCT/US2015/011467, Written Opinion dated Mar. 26, 2015", 8 pgs.

(56) References Cited

OTHER PUBLICATIONS

"International Application Serial No. PCT/US2015/011468, International Preliminary Report on Patentability dated Jul. 28, 2016", 9 pgs.

"International Application Serial No. PCT/US2015/011468, International Search Report dated Mar. 30, 2015", 5 pgs.

"International Application Serial No. PCT/US2015/011468, Written Opinion dated Mar. 30, 2015", 7 pgs.

"Japanese Application Serial No. 2016-547078, Office Action dated Jul. 4, 2017", 7 pgs.

"Japanese Application Serial No. 2016-547080, Office Action dated Jun. 27, 2017", w/o translation, 6 pgs.

Fisher, Karen M., et al., "Blocking central pathways in the primate motor system using high-frequency sinusoidal current", J Neurophysiol 113(5): 1670-1680, Mar. 1, 2015.

Franke, Manfred, "Translating Electric KHFAC and DC Nerve Block from Research to Application", Thesis • May 2014, 199 pages.

Franke, Manfred, et al., "Translating Electric KHFAC and DC Nerve Block from Research to Application", PhD Thesis, Case Western Reserve University, (May 2014), 199 pgs.

Ishii, Koji, et al., "Effects of Neostigmine on Bronchoconstriction With Continuous Electrical Stimulation in Rats", Journal of Anesthesia, Springer-Verlag, TO, vol. 26, No. 1, (Nov. 1, 2011), 80-84.

Stretton, C, et al., "Sensory Nerve Depletion Potentiates Inhibitory Non-Adrenergic, Non-Cholinergic Nerves in Guinea-Pig Airways", European Journal of Pharmacology, Elsevier Science, NL, vol. 184, No. 2-3, (Aug. 10, 1990), 333-337.

Wedensky, N.E., "Die Erregung, Hemmung und Narkose (The excitation, inhibition and Narkose)", Archiv für die gesamte Physiologie des Menschen und der Tiere, 1903. 100: p. 1-144 (With Machine Translation).

Wedensky, N.E., "Ueber einige Beziehungen zwischen der Reizstarke und der Tetanushohe bei indirecter Reizung Over some relations between the attraction strength and the Tetanushöhe when indireeter provoking", Archiv für die gesamte Physiologie des Menschen und der Tiere of Dr. E.F.W. Pflüger, 37: p. 69-72, Dec. 1885 (With Machine Translation).

"U.S. Appl. No. 14/597,112, Advisory Action dated Oct. 20, 2017", 4 pgs.

"U.S. Appl. No. 14/597,112, Pre-Appeal Brief Request filed Nov. 13, 2017", 5 pgs.

"U.S. Appl. No. 14/597,112, Response filed Sep. 12, 2017 to Final Office Action dated Jul. 12, 2017", 11 pgs.

"U.S. Appl. No. 14/597,131, Examiner Interview Summary dated Oct. 25, 2017", 4 pgs.

"U.S. Appl. No. 14/597,131, Pre-Appeal Brief Request filed Nov. 24, 2017", 5 pgs.

"U.S. Appl. No. 14/597,145, Advisory Action dated Nov. 22, 2017", 6 pgs.

"U.S. Appl. No. 14/597,145, Examiner Interview Summary dated Oct. 31, 2017", 3 pgs.

"U.S. Appl. No. 14/597,145, Final Office Action dated Aug. 30, 2017", 14 pgs.

"U.S. Appl. No. 14/597,145, Non Final Office Action dated Jan. 9, 2018", 15 pgs.

"U.S. Appl. No. 14/597,145, Response filed Oct. 30, 2017 to Final Office Action dated Aug. 30, 2017", 12 pgs.

"U.S. Appl. No. 14/597,145, Response filed Nov. 30, 2017 to Advisory Action dated Nov. 22, 2017", 14 pgs.

"Japanese Application Serial No. 2016-547078, Response filed Dec. 27, 2017 to Office Action dated Jul. 4, 2017", w/ claims in English, 11 pgs.

"Japanese Application Serial No. 2016-547080, Response filed Oct. 13, 2017 to Office Action dated Jun. 27, 2017", w/ claims in English, 10 pgs.

"U.S. Appl. No. 14/597,131, Appeal Brief filed Mar. 16, 2018", 24 pgs.

"U.S. Appl. No. 14/597,145, Examiner Interview Summary dated Apr. 16, 2018", 4 pgs.

"Japanese Application Serial No. 2016-547080, Office Action dated Apr. 3, 2018", w/ English translation, 9 pgs.

\* cited by examiner

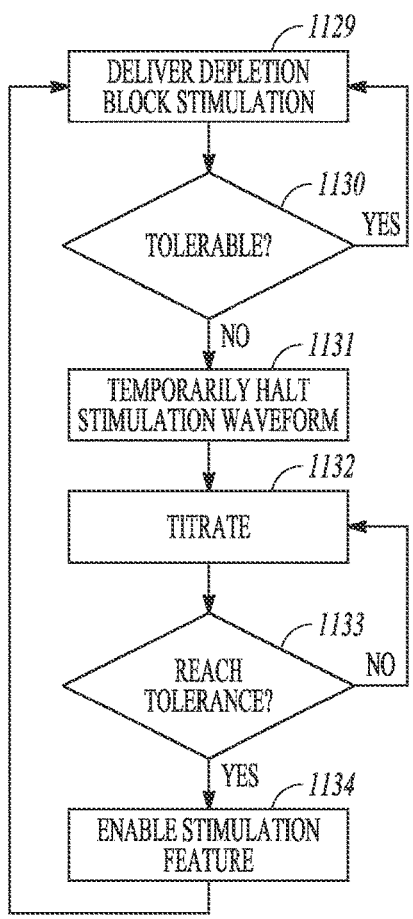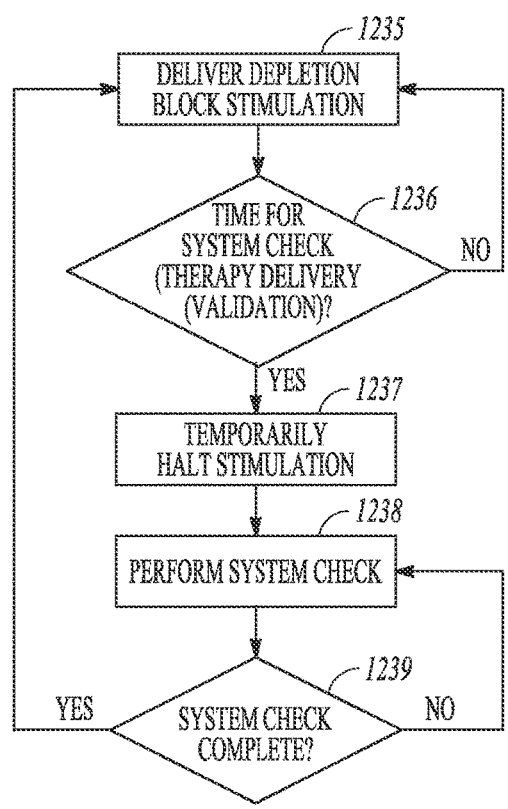
*FIG. 11*  *FIG. 12*

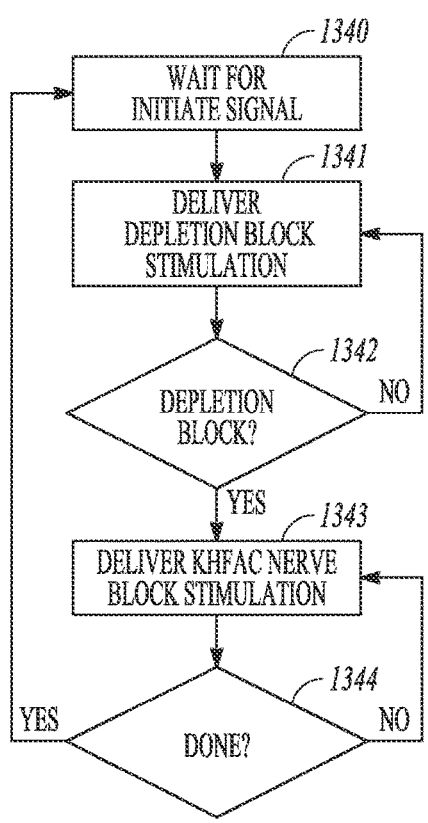
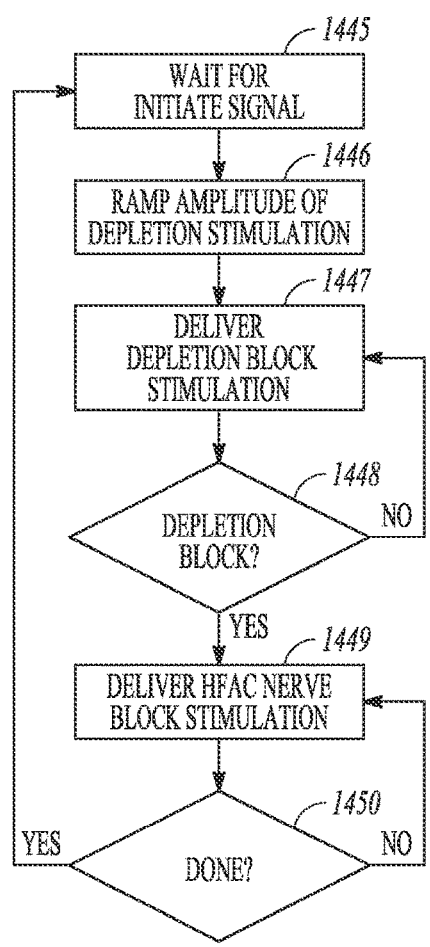
*FIG. 13*   *FIG. 14*

PROXIMAL NERVE
DEPLETION BLOCK

DEPLETION BLOCK TO BLOCK NERVE COMMUNICATION

CLAIM OF PRIORITY

This application claims the benefit of priority under 35 U.S.C. § 119(e) of U.S. Provisional Patent Application Ser. No. 61/928,725, filed on Jan. 17, 2014, which is herein incorporated by reference in its entirety.

CROSS REFERENCE TO RELATED APPLICATIONS

The following commonly-assigned U.S. patent application are related, are all filed on the same date as the present application, and are all herein incorporated by reference in their entirety: "Systems and Methods for Selective Stimulation of Nerve Fibers in Carotid Sinus," Ser. No. 61/928,707 filed on Jan. 17, 2014; "Systems and Methods for Delivering Pulmonary Therapy," Ser. No. 61/928,714, filed on Jan. 17, 2014; and "Selective Nerve Stimulation Using Presynaptic Terminal Depletion Block," Ser. No. 61/928,732, filed on Jan. 17, 2014.

TECHNICAL FIELD

This document relates generally to medical devices, and more particularly, to systems, devices and methods for blocking nerve communication.

BACKGROUND

Neural stimulation has been proposed as a therapy for a number of conditions. Neural stimulation may be delivered to modulate the autonomic system, which may be referred to as an autonomic modulation therapy (AMT). Examples of AMT include therapies for respiratory problems such as sleep disordered breathing, blood pressure control such as to treat hypertension, cardiac rhythm management, myocardial infarction and ischemia, heart failure (HF), and modulation of the cholinergic anti-inflammatory pathway. For example, therapies to treat epilepsy, depression, pain, migraines, eating disorders and obesity, and movement disorders may include stimulation of a vagus nerve.

For some therapies it is desirable to block or inhibit action potentials from propagating in nerve axons. Neural stimulation may be delivered to block nerve traffic. For example, kilohertz high frequency alternating current (KHFAC) or direct current (DC) may be used to block action potentials. However, both KHFAC and DC blocking has some limitations. For example, KHFAC blocks cause an intense burst of firing in the nerve when first initiated, which is likely to produce an uncomfortable sensation of that may last from milliseconds to more than 30 seconds. Additionally, DC nerve blocks are unsafe for the nerve for chronic applications because they deliver unrecoverable charge to the neural tissue.

SUMMARY

Various embodiments described may relate to methods and systems that provide a full or partial depletion block used to block or inhibit nerve communication without the disadvantages associated with KHFAC or DC blocking techniques. An electrical signal may be applied to at least some nerve fibers at a stimulation intensity that exceeds the stimulation threshold for at least some of the nerve fibers within a nerve to quickly deplete neurotransmitters from a presynaptic terminal of axons corresponding to the nerve fibers that have been stimulated at an intensity that exceeds their respective stimulation threshold. The stimulation activates the action potentials on the nerve fibers, but the frequency of the stimulation blocks or inhibits communication from the presynaptic terminal to the postsynaptic membrane. Further, the depletion block is quickly reversed by terminating the application of the electrical signal as the neurotransmitter supply is quickly restored.

An example of a method may create a depletion block at a presynaptic terminal of an axon. Creating the depletion block may include delivering a series of electrical pulses to the axon at a pulse frequency where the pulse frequency is within a range between about 100 Hz to about 1000 Hz (e.g. 100 Hz to 1000 Hz or frequencies effectively near that range to provide the depletion block). An example of a method may create a depletion block at a presynaptic terminal of an axon. Creating the depletion block may include delivering a series of electrical pulses to the axon at a pulse frequency where the pulse frequency is within a range between about 100 Hz to about 1000 Hz (e.g. 100 Hz to 1000 Hz or frequencies near that range to provide the depletion block). Delivering the series of electrical pulses to the axon causes action potentials to propagate through the axon at a frequency corresponding to the pulse frequency. The frequency of the action potentials causes the depletion block within one second of initiation of the series of electrical pulses. The method may further include removing the depletion block at the presynaptic terminal. Removing the depletion block may include stopping the series of electrical pulses from being applied to the axon to remove the depletion block within 1 second after stopping the series of electrical pulses.

An example of a system may include a depletion block neural stimulator and a depletion block controller. The depletion block neural stimulator may be configured to deliver a depletion block stimulation to a nerve. The depletion block stimulation may include a series of pulses at a pulse frequency within a range between about 100 Hz to about 1000 Hz (e.g. 100 Hz to 1000 Hz or frequencies effectively near that range to provide the depletion block). The depletion block controller may be configured to communicate with the depletion block neural stimulator and control the depletion block stimulation. The depletion block controller may be configured to receive a start depletion block signal and respond to the received start depletion block signal by initiating the delivery of the depletion block stimulation to the nerve, and the depletion block controller may be configured to receive a stop depletion block signal and respond to the received stop depletion block signal by terminating the delivery of the depletion block stimulation to the nerve. This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 11 illustrates, by way of example and not limitation, an embodiment of a process for titrating a presynaptic terminal depletion block.

FIG. 12 illustrates, by way of example and not limitation, an embodiment of a process for validating a presynaptic terminal depletion block.

FIG. 13 illustrates, by way of example and not limitation, an embodiment of a process for delivering a presynaptic terminal depletion block with a high frequency AC nerve block.

FIG. 14 illustrates, by way of example and not limitation, an embodiment of a process for ramping up a presynaptic terminal depletion block in preparation with a high frequency AC nerve block.

DETAILED DESCRIPTION

Figure 1:
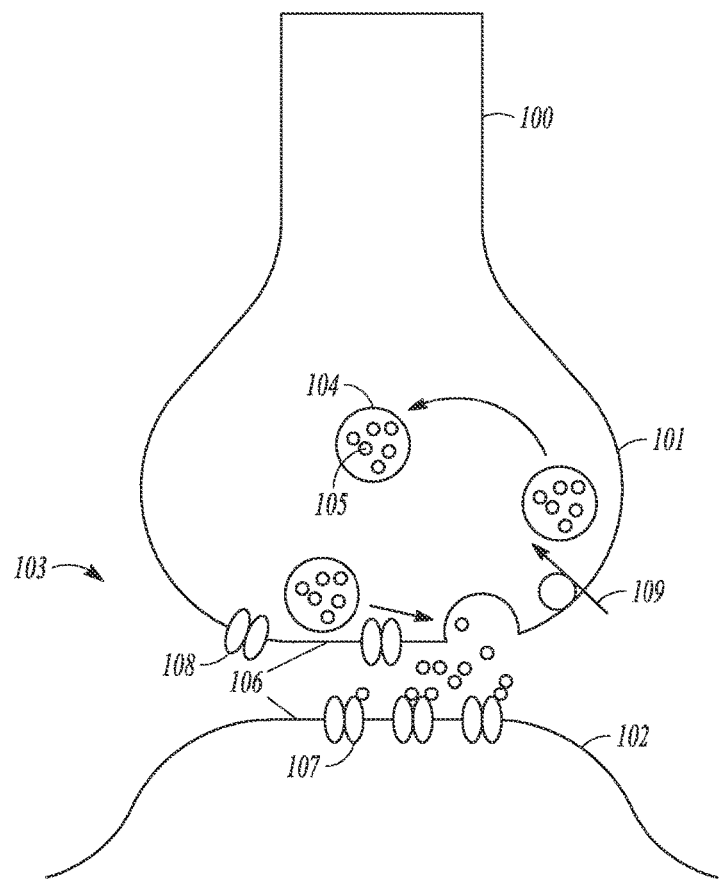
FIG. 1 illustrates neural activity at a synapse between a nerve and another membrane.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Nerve fibers, also referred to as axons, are projections from nerve cells. A nerve fiber connects a nerve cell to another nerve cell or to muscle or to gland cells at synapses, which are structures that permit nerve cells to pass an electrical or chemical signal to other cells. Nerve fibers includes A fibers, B fibers, and C fibers. A fibers can be both motor (efferent) or sensory (afferent). A fibers are the largest and, generally, the first captured as stimulation amplitude increases. Motor fibers innervate muscle tissue. For example, stimulation of the vagus nerve in the cervical region may excite laryngeal muscle fibers which causing laryngeal activation which may be used as a marker for capture of the vagus nerve. B fibers are smaller and next to be captured when increasing current amplitude. These are typically efferent parasympathetic and sympathetic fibers. These B fibers may be a target for an autonomic neural stimulation therapy. C fibers are the smallest and associated with pain and other sensory information. It has been observed that thicker nerve fibers are generally activated before thinner nerve fibers. Thick nerve fibers have longer sections of myelin sheaths between the nodes of Ranvier where the depolarization occurs and thus the change in electric field they experience is greater. It is currently believed that the vagus nerve includes the fiber types and sizes illustrated in Table 1, and it is further believed that the majority of the fibers are C fibers.

TABLE 1

Vagal Nerve Fibers

| Fibers | Origin | Size (um) | Conduction Velocity (m/s) | Innervation |
| --- | --- | --- | --- | --- |
| Aα | Motor | 13-20 | 80-120 | Larynx |
| Aγ | Motor | 5-8 | 4-24 | |
| Aα | Sensory | 13-20 | 80-120 | All organs |
| Aβ | Sensory | 6-12 | 33-75 | larynx and airways |
| Aδ | Sensory | 1-5 | 3-30 | lungs, heart |
| B (pre-g) | Efferent | 1-5 | 3-15 | stomach, pancreas |
| C (pos-g) | Efferent | 0.2-1.5 | 0.5-2 | bladder |
| C | Sensory | 0.2-1.5 | 0.5-2 | |

Some proposed autonomic neural stimulation therapies attempt to capture as many nerve fibers in the vagus nerve as possible by titrating amplitude up as high as tolerable. In general terms vagal stimulation may first capture A motor and large sensory nerves fibers, then small sensory and B parasympathetic nerve fibers. This order is a general order because fibers that are closer to the electrodes experience a stronger electric field and are activated before fibers that are further away, and further these fiber types overlap in their size. The fibers that drive heart rate down are the smallest B efferent parasympathetic fibers. These B efferent parasympathetic fibers are the smallest of the myelinated fibers, as the C fibers are unmyelinated. Neural stimulation that causes a heart rate response indicates that the B efferent parasympathetic fibers have been captured and that the other larger fiber types are also being captured.

FIG. 1 illustrates neural activity at a synapse between a nerve and another membrane. An action potential propagates electrically down nerve axon 100 until it reaches a nerve ending, which may be referred to as a presynaptic terminal 101. The presynaptic terminal communicates with a postsynaptic membrane 102 of a target cell. The target cell may be another nerve or a muscle or gland. This membrane-to-membrane junction of the presynaptic terminal and the target cell is referred to as a synapse 103. A type of synapse is an electrical synaptic junction where the presynaptic terminal electrically communicates with the postsynaptic membrane using ions or small molecules that pass through channels from one cell to the next. Another type of synapse is a chemical synaptic junction, where neurotransmitters are used to transmit between cells. The presynaptic area 101 has a large number of synaptic vesicles 104 that contain neurotransmitter chemicals 105. The action potentials that propagate to the presynaptic terminal 101 drives a chemical reaction in the presynaptic terminal that releases neurotransmitters into the extracellular space which may be referred to as a synaptic cleft 106. The neurotransmitters cross the synaptic cleft between the presynaptic and postsynaptic terminals. The neurotransmitter start a chain of reaction in receptors 107 of either the post-synaptic membrane 102 (another neuronal cell) or the muscle cells (neuromuscular junction) that trigger either the firing of an action potential in the post-synaptic neuron or the muscular contraction if the synapse ends in a neuromuscular junction. For example, where the target cell is a muscle and the synapse is a neuromuscular junction, the neurotransmitter acetylcholine (Ach) causes a rapid contraction of the target muscle cell. At a neuromuscular junction, the action potential travels to the neuromuscular synaptic junction, causing calcium ions to flow through voltage-gated calcium channels 108 which release Ach from the presynaptic terminal into the extracellular space to be received by postsynaptic receptors in the membrane of the target muscle cell. The presynaptic terminal has a neurotransmitter re-uptake pump 109 that replenishes the presynaptic terminal with synaptic vesicles of neurotransmitters.

The present inventors have observed that continual communication across this synaptic cleft 106 appears to require a minimal amount of time between action potentials in the nerve as the present inventors have observed that postsynaptic receptors do not trigger action potentials if the pre-synaptic action potentials arrive close to each other. For example, a neural stimulation signal may be within a range from about 0.25 Hz to 50 Hz, or may be within a range of about 2 Hz to about 20 Hz, or may be about 20 Hz. At higher frequencies (e.g. about 100 Hz to 1 kHz), it was observed that the presynaptic terminal was unable to communicate across the synaptic cleft even though action potentials continued to propagate through the axon. The present inventors tested this reaction time using different stimulation frequencies. Generally, at frequencies within the range of 100 Hz to 1 kHz, every neural stimulation pulse in a neural stimulation signal will generate an action potential. As will be understood by those of ordinary skill in the art, an exception to this general statement is neural stimulation configured to block nerve traffic through a particular electrode configuration or stimulation frequency. Thus, for frequencies within the range of 100 Hz to 1 kHz, higher stimulation frequencies will generate more stimulation pulses in a given period of time, and may generate more corresponding action potentials in the nerve during the period of time. The frequencies used to obtain this depletion block are lower than the high frequency AC nerve block that blocks action potentials from propagating down the nerve. At frequencies higher than 1 kHz, for example, the stimulation blocks the nerve from conducting the action potentials. In contrast, the depletion block is delivered at frequencies below 1 kHz and thus does not stop the action potentials from propagating down the nerve to the presynaptic terminal, but rather depletes the presynaptic terminal so it is no longer able to communicate across the synaptic cleft to receptors of another cell.

Figure 2:
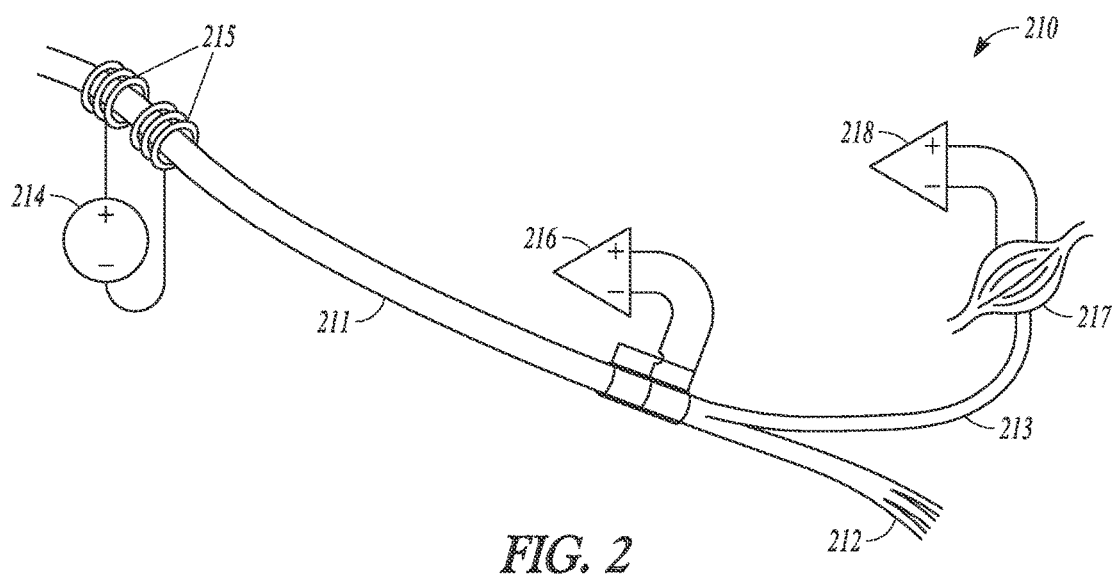
FIG. 2 illustrates an experimental setup used to observe a presynaptic depletion block.

FIG. 2 illustrates an experimental setup 210 used to observe a presynaptic depletion block. A cervical vagus nerve 211 branches into the thoracic branch 212 and the recurrent laryngeal nerve 213. The illustrated experimental setup was used to stimulate the cervical vagus nerve 213 using a current source 214 and helical electrodes 215 in a bipolar arrangement, to monitor neural activity before the cervical vagus nerve 211 branches into the recurrent laryngeal nerve branch 213 and the thoracic branch 212 using an electroneurography (ENG) monitor 216, and to monitor vibration of the laryngeal muscles 217 using an electromyography (EMG) monitor 218. This set up was used to observe that action potentials from stimulation were still sensed by the ENG, but laryngeal vibrations were not sensed by the EMG 218.

Figure 3:
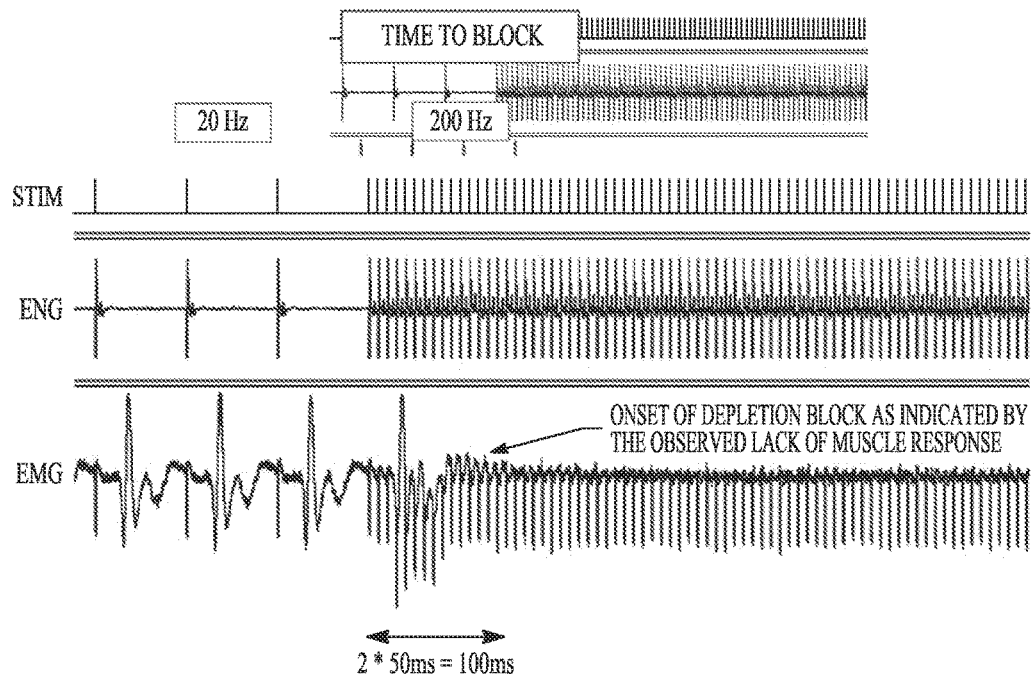
FIG. 3 illustrates the observed relationship between the stimulus signal and the recorded ENG and EMG signals when the stimulus changes from 20 Hz to 200 Hz, and includes the observed time to deplete the presynaptic terminal and block the synaptic junction.

FIG. 3 illustrates the observed relationship between the stimulus signal and the recorded ENG and EMG signals when the stimulus changes from 20 Hz to 200 Hz, and includes the observed time to deplete the presynaptic terminal and block the synaptic junction. During the 20 Hz stimulation, both the ENG and EMG signals follow the stimulus signal. The high peaks in both ENG and EMG signals reflect the stimulation artifact. However, during the 200 Hz stimulation, the ENG response is still present after the stimulus signal, but the EMG signal quickly subsides. It has been observed that the EMG signal subsides after an onset response of about 100 ms. Rather, after a brief transitional period after the stimulus changes to 200 Hz, only the artifact from charge-balancing is seen in the EMG waveform. Thus, the axons in the nerve continue to be active by propagating action potentials, but the communication across the synaptic cleft is reduced or stopped after the presynaptic terminal has been depleted from its ability to communicate. As illustrated, this synaptic junction block occurs very quickly (e.g. 50 to 100 ms after the 200 Hz signal is applied), as soon as the propagated pulses received at the presynaptic terminal deplete the presynaptic terminal. Again, it is currently believed that the presynaptic terminal is depleted from its ability to communicate because the presynaptic terminal has been depleted of the neurotransmitters and/or calcium. It does not appear that the physiological reuptake process that restores neurotransmitters and/or calcium in the presynaptic terminal can keep up with the initial transmission of the neurotransmitters from the 200 Hz stimulation. An onset period can also be observed after the frequency shift where the muscle appears to contract strongly for a short time and then relaxes. Table 2 shows the time needed for the muscles to stop contracting.

Figure 4:
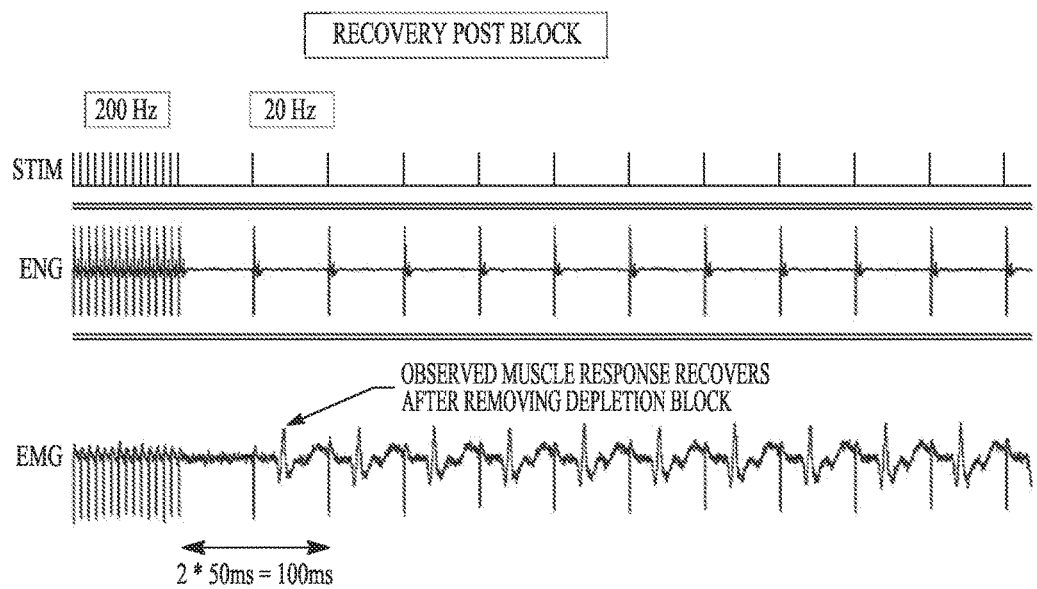
FIG. 4 illustrates the relationship between the stimulus signal and the recorded ENG and EMG signals when the stimulus changes from 200 Hz to 20 Hz.

FIG. 4 illustrates the relationship between the stimulus signal and the recorded ENG and EMG signals when the stimulus changes from 200 Hz to 20 Hz. The synaptic junction block occurs when the stimulus is delivered at 200 Hz. During this time, the ENG is still present following the stimulus artifact signal but the EMG response is not present.

This indicates that the stimulus is capturing the nerve and causing action potentials to propagate through the axon. Every pulse in the stimulation causes a respective action potential in the nerve fiber. However, the laryngeal muscle is not stimulated because of the presynaptic depletion at 200 Hz that causes the synaptic junction block. The 200 action potentials per second deplete the ability of the presynaptic terminal to communicate across the synaptic cleft. When the stimulus changes from 200 Hz to 20 Hz, however, the ENG response continues to be present following the stimulus pulse at the lower frequency as every pulse in the stimulation causes a respective action potential in the nerve fiber. The EMG now reappears right after the stimulus pulse just after a brief transitional period after the stimulation frequency changes to 20 Hz. The ability of the presynaptic terminal to communicate across the synaptic cleft is not depleted by 20 pulses per second. Thus, as illustrated, the synaptic junction block can be removed very quickly (e.g. 50 ms to 100 ms after the 20 Hz signal is applied), which is believed to be the physiological response time for restoring neurotransmitters and/or calcium in the presynaptic terminal.

Table 2 illustrates that certain frequencies can turn the depletion block of the synaptic junction on/off more quickly than other frequencies. Data suggest that frequencies greater than about 200 Hz provide a fast depletion block, whereas frequencies between about 100 to about 150 Hz provides slower depletion blocks. Frequencies below 100 Hz tend not be effective to provide the depletion block, as the frequency does not exceed the ability of the presynaptic terminal to restore its ability to communicate from the presynaptic terminal across the synaptic cleft to the target cell. In a neural muscular junction, for example, frequencies less than about 100 Hz cause tetanic contraction; frequencies between about 100 to about 150 Hz causes a 90% depletion block in about 10 seconds to 4 seconds; a frequency between about 200 Hz to 1000 Hz causes a 90% depletion block. Nerve conduction block where the stimulation arrests the action potentials propagating down the nerve has been observed at frequencies as low as 1 kHz but more typically between 5-10 kHz.

TABLE 2

| | Freq (Hz) | Time to 90% Block (sec) | | Percentage of unblocked EMG (%) | |
|---|---|---|---|---|---|
| | | mean | stdev | mean | stdev |
| Activation | 40[1] | — | — | 110 | 13.18 |
| | 70[1] | — | — | 39 | 8.42 |
| Slow Block | 100*,[2] | 10.74 | 2.2 | 8.2 | 3.77 |
| | 130[1] | 9.33 | 0.55 | 4.38 | 1.06 |
| | 150[2] | 4.43 | 2.59 | 3.88 | 1.13 |
| Fast Block | 200[2] | 0.53 | 0.16 | 2.25 | 1.04 |
| | 260[1] | 0.16 | 0.05 | 0.75 | 0.89 |
| | 300[2] | 0.13 | 0.05 | 1.13 | 1.13 |
| | 400[1] | 0.14 | 0.05 | 0.63 | 0.74 |

Randomized study; n = 8 (100 Hz: n = 5), data from 2 * N = 1

Stimulation of axons within a range generally below 100 Hz (e.g. about 50 Hz) may cause a tetanic contraction of the muscle. Eventually, the muscle may tire and no longer respond to additional stimulation. Although this may and is expected to change from application to application, these stimulation parameters are expected to be available in current devices at reasonable energy consumption costs. A-fibers were responsible for the laryngeal motor fibers recorded via EMG. Small parasympathetic efferent B-fibers have a higher activation threshold are typically are responsible for heart rate control in the SA node. This example showed that NMJ block, just as activation via electrical stimulation, is graded to the size of the fiber axon being targeted. As illustrated in Table 2, the speed of the depletion block depends on the frequency of the stimulation, where higher frequencies within the range of about 100 Hz to about 1 kHz will provide the neurotransmitter block more quickly than the lower frequencies within that range. According to some embodiments, the depletion block may be implemented by a process that initiates the depletion block at a relatively high frequency (e.g. about 200 Hz to 300 Hz) to achieve fast depletion (e.g. about 50 ms or less), and then subsequently lower the frequency of the depletion block stimulation to about 100 Hz to maintain the block. As the lower frequency stimulation delivers fewer pulses, the lower frequency depletion block is more energy efficient than the higher frequency depletion block. If the depletion block was started at about 100 Hz rather than 200 Hz, it would take longer to achieve the depletion block. Based on current observations, it is believed that the depletion block at 100 Hz will take about 5 seconds to 10 seconds. The use of two (or more) stages of frequencies can be used to obtain benefits of each frequency, such as inducing depletion block relatively quickly using one frequency and then maintaining depletion block relatively efficiently using another frequency. A therapy may be delivered during a time period after the depletion block is created and before the depletion block is removed. Some embodiments may create a depletion block with a first frequency, transition to maintain the depletion block with a second frequency, deliver a therapy, and remove the second frequency depletion block after the therapy deliver is complete or after any therapy withdrawal window is over.

Figure 5A:
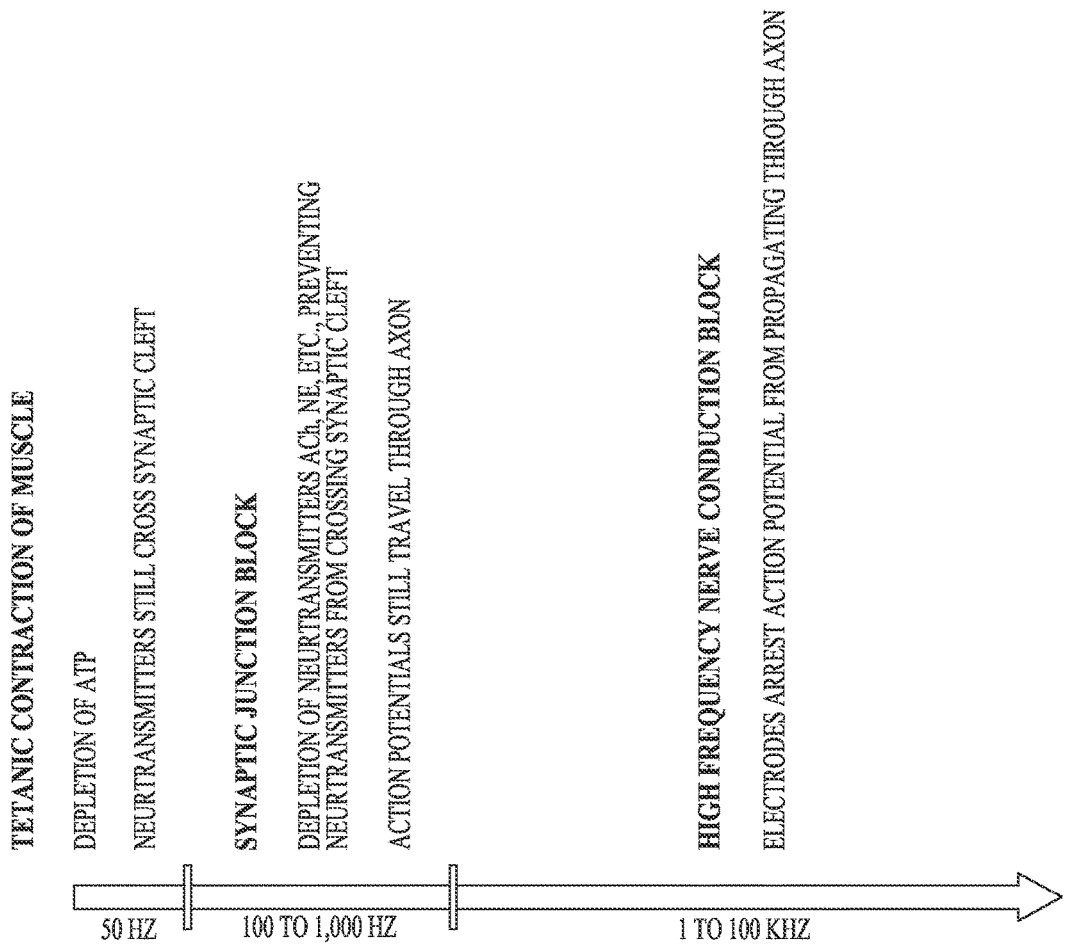
FIGS. 5A and 5B illustrate the response of a neural muscular junction to different stimulation frequencies.

FIG. 5A illustrates the response of a neural muscular junction to different stimulation frequencies. The neural muscular junction is a type of synaptic junction where nerve communicates with muscle. Stimulation of axons within a range generally below 100 Hz (e.g. about 50 Hz) may cause a tetanic contraction of the muscle. Eventually, the muscle may fatigue and no longer respond to additional stimulation. The presynaptic terminal is depleted from its ability to communicate across the synaptic cleft at stimulation frequencies within a range from about 100 Hz to about 1000 Hz. This frequency may be high enough to cause neurotransmitters and/or calcium from being replenished quick enough for subsequent action potentials in the stimulation. Even when the neurotransmitters are blocked at the neurotransmitters, action potentials may still propagate through axons on the presynaptic axon. Stimulation that captures an axon at frequencies higher than 1 kHz will provide a nerve block that arrests action potentials from propagating in the axon.

Figure 5B:
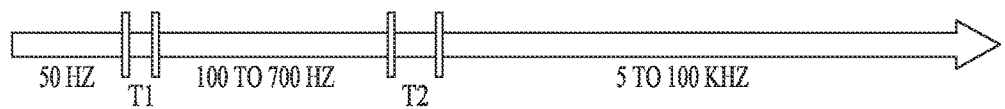

It is noted that FIG. 5A is a simple illustration of frequency ranges, and that these ranges may vary for different applications. FIG. 5B provides another illustration of a response of a neural muscular junction to different stimulation frequencies. FIG. 5B illustrates a transition period T1 between the activation and depletion block ranges. Transition period T1 may depend on the transmitter and the synaptic end-organ, and may range from about 70 to 130 Hz. FIG. 5B also illustrates a transition period T2 between the depletion block and conduction block ranges that may provide a combined depletion and conduction block.

Some characterizations of depletion block, combined depletion and conduction block, and high frequency kHz conduction blocks are provide below. For example, a depletion block has a lower frequency and thus lower power requirements, has a relatively fast block (<100 ms) and a relatively fast recovery (<100 ms over 50% and 10 seconds 100%). For example, a combined depletion and conduction block (e.g. around 1 kHz) may block slow fibers extremely fast due to conduction block, may be initiated with a high kHz frequency and then lowered to keep the block at lower frequencies, may block slower fibers in less than 7 ms, and may have a faster recovery than the higher frequency kHz blocks. For example, a high frequency kHz conduction block is fast (e.g. on: <7 ms an off: <10 ms), but is more energy intensive due to higher frequencies and current requirements.

For example, a kHz conduction block may be observed with a lower boundary of about 1 kHz to 5 kHz rather than the simply illustrated 1 kHz. Additionally, the upper boundary of a depletion block may be about 2 kHz rather than the simply illustrated 1 kHz. Further, the frequencies for which stimulation transitions from depletion to conduction depends on the nerve fibers and end plate. Fast a-fibers have higher conduction and firing rates, so they will not necessarily block at 1 kHz, and slower fibers will block at lower frequencies (e.g. 600 Hz). Thus, there may be a nerve stimulation frequency band within which most fibers can be activated, a depletion block frequency band for which most fibers may be depleted, and a kHz conduction block frequency band for which most fibers have their action potentials blocked. By way of example, the nerve stimulation frequency band may extend up to about 50 Hz, the depletion block frequency band may extend between about 100 Hz to about 700 Hz, and the kHz conduction block frequency band may extend from about 5 kHz to 100 kHz. There may be transition frequencies between the bands, such as a transition between about 50 Hz to about 100 Hz or between about 70 Hz to 130 Hz for example and another transition between about 700 Hz to about 5 kHz. The response of the nerve to the stimulation frequency appears to depend on the transmitter and the synaptic end organ. Thus, different types of fibers may react differently for frequencies within the transition frequencies. By way of example, one frequency may cause an activation or neural stimulation of some fibers, and cause a depletion block in other fibers. The stimulation may be limited to specific fibers by the diameter or origin of the fibers or the location of the electrodes. For example, a frequency of the depletion block stimulation may be found to discriminate between afferent and efferent nerve fibers, or to discriminate between different fibers that emit different types of neurotransmitters. Such a frequency capable of providing both depletion block and activation/stimulation may be found in a transition region, but also may be found in one of the frequency bands such as within the depletion block frequency band.

Various embodiments may use a depletion block at the synaptic junction to provide selective fiber communication. The amplitude of the depletion block pulses can be controlled to be greater than only the stimulation threshold for only some of the nerve fibers. Thus, although all fibers may be stimulated with another stimulation signal that causes action potentials to propagate, the presynaptic terminal for some of the fibers are quickly depleted from their ability to communicate across the synaptic junction because the frequency of the stimulation causes the depletion block. Stimulation at these frequencies (e.g. about 100 Hz to about 1000 Hz) appears to be too fast for a neural muscular junction to replenish Ach or to otherwise replenish its ability to communicate with the muscle cell. Various stimulation waveforms may be used including non-sinusoidal or sinusoidal waveforms. Non-sinusoidal waveforms may include rectilinear pulses, charge balanced waveforms that may include biphasic rectangular pulses, quasi-trapezoidal for uni-directional application, and pulsed triangular.

The depletion block for a neural muscular junction results from the high rate of firing which is about three to five times the maximum tetanic firing rate of the neural muscular junction. That is, the frequency of the stimulation signal is outside of the ability of the physiological system to trigger the muscular contraction. The observed block is attributable to a depletion of the junction but not fatigue of the muscle. Thus, a benefit of the depletion block applied to neural muscular junctions is that the depletion block does not cause muscle fatigue or tetanic contraction. The neuromuscular depletion block is quick reversible by stopping stimulation. Neural stimulation that elicits nerve traffic (e.g. activates nerve fiber(s)) and a desired physiological response as part of neural stimulation therapy may be referred to simply as nerve stimulation or as a low frequency stimulation (e.g. about 20 Hz); whereas in comparison a depletion frequency may be referred to as high frequency (e.g. about 200 Hz). A "high amplitude, low frequency" (HALF) stimulation signal may exceed a stimulation threshold and thus may be used to recruit both small and big fibers. As such, a HALF signal may be used to obtain the desired effect of the stimulation by capturing all the necessary A sensory and B efferent fibers. A "small amplitude, high frequency" (SAHF) stimulation signal may be set at an amplitude that it only exceeds a smaller stimulation threshold and thus only recruits some of the fibers with the lower stimulation threshold (e.g. bigger fibers or fibers closer to the stimulation electrode(s)), while leaving other fibers with a higher stimulation threshold (e.g. smaller fibers or fibers further away from the stimulation electrode(s)) still excitable with the HALF stimulation. The depletion block stimulation cancels the effectiveness of all signals that are evoked at lower frequencies (e.g. 20 Hz) with the same or lower amplitude. SAHF may be used to achieve the neurotransmitter depletion block of the large fibers which are the fibers with relatively low stimulation thresholds but not the smaller fibers which are the fibers with relatively high stimulation thresholds. In some embodiments, the higher frequency depletion block stimulation may be delivered using the same or approximately the same high amplitude as the low frequency stimulation to reduce or modulate the effect of the applied therapy using the low frequency stimulation.

Figure 6A:
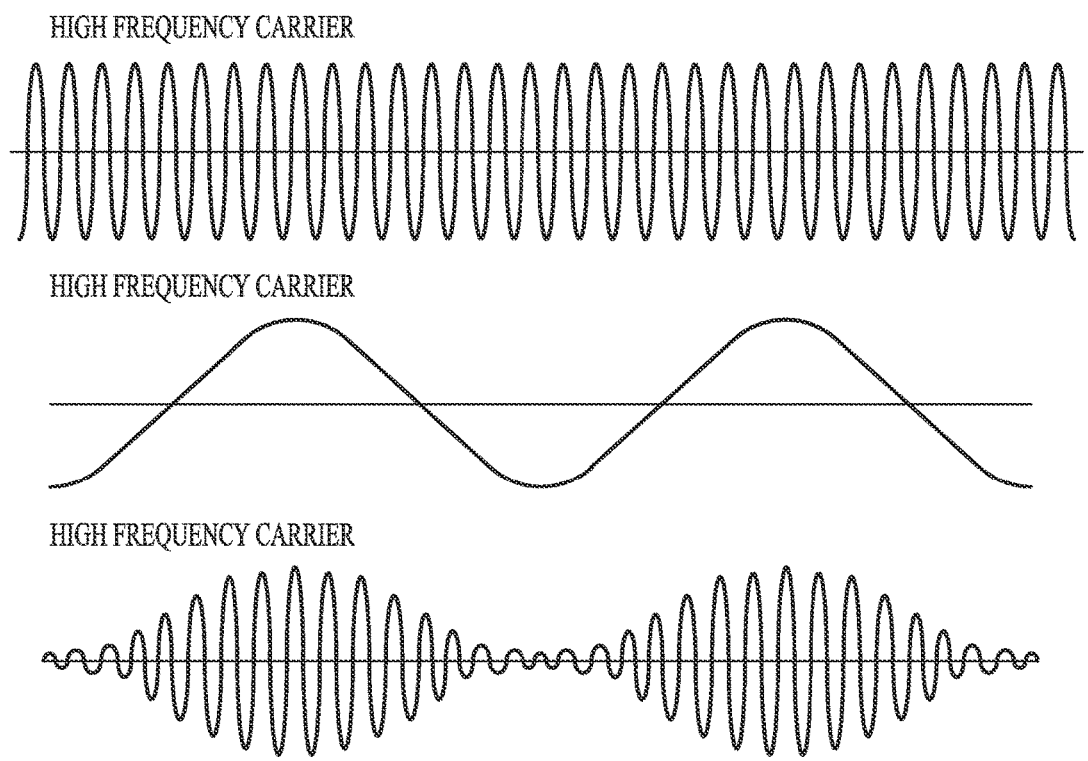
FIGS. 6A-6B illustrate, by way of example and not limitation, some waveforms that may be used to deliver low frequency therapeutic neural stimulation and higher frequency depletion block stimulation at the same amplitude.
Figure 6B:
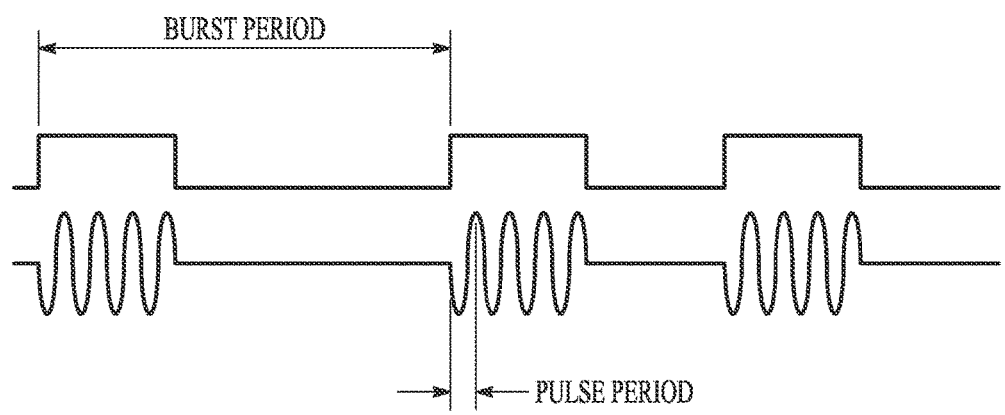

In some embodiments, the high frequency depletion stimulation may be delivered using the same or approximately the same high amplitude as the low frequency stimulation to reduce or modulate the effect of the applied therapy using the low frequency stimulation. FIGS. 6A-6B illustrate, by way of example and not limitation, some waveforms that may be used to deliver low frequency therapeutic neural stimulation and higher frequency depletion block stimulation at the same amplitude. FIG. 6A illustrates an amplitude modulated signal where a high frequency carrier signal is at a frequency (e.g. on the order of 200 Hz) effective for providing a depletion block, and a low frequency modulating signal is at a frequency (e.g. on the order of 20 Hz) effective for eliciting nerve traffic for a neural stimulation therapy. FIG. 6B illustrates trains of pulses, where the pulse frequency is effective for providing a depletion block (e.g. on the order of 200 Hz) and the burst frequency is effective for providing stimulating a nerve to elicit a neural response for a therapy (e.g. on the order of 20 Hz).

The current amplitude and the pulse width control whether an axon is depolarized, and the frequency of the stimulation controls whether the neurotransmitters are depleted at the nerve ending. The current amplitude and pulse width may be controlled to select only larger fibers for the neural muscular junction block. For example, the current amplitude and pulse width may be controlled to deplete neurotransmitters from the A fibers and not the smaller fibers, or may be controlled with higher amplitudes and/or wider pulse widths to deplete both A and B fibers. By way of example and not limitation, a full neurotransmitter block for intended fibers may be ensured by acquiring a recruitment curve. The recruitment curve may identify the activation threshold and saturation threshold for the neural target. The recruitment curve may illustrate an increase in activity with increasing current amplitude, and may then illustrate a plateau where the activity does not significantly increase with increasing current amplitude. The activation threshold reflects where the nerve activity begins to increase with increasing current amplitude, and the saturation threshold reflects where the nerve activity does not significantly increase in response to further increases in current amplitude. The current amplitude for the depletion block stimulation may be determined based on the activation threshold, as it may be set at a margin higher than the activation threshold. The saturation threshold indicates a threshold where all or almost all of the nerve fibers propagate action potentials. The current amplitude for the depletion block stimulation may be determined based on the saturation threshold of the fibers that are intended to be blocked. By way of example, the amplitude of the depletion stimulation signal may be set at approximately the saturation threshold of the fibers that are intended to be blocked, or may be set at a margin higher than the saturation threshold of the fibers, or may be set at a margin lower than the saturation threshold to provide a partial block.

A procedure can be implemented to determine each individual patient's selective fiber stimulation therapy profile, as there may be patient variation or variations resulting from electrode spacing from nerves fibers. The particular procedure will depend on the particular neural target that is stimulated, as the nerve fibers in different neural targets innervate different portions of the body. For example, if a cervical vagus nerve is targeted, the patient's selective fiber stimulation therapy profiled may be determined by observing laryngeal vibration as well as blood pressure and heart rate fluctuations. Thus, various embodiments for providing a depletion block may first find an activation threshold and saturation threshold for a neural target. The current amplitude may be selected to be above the saturation threshold of the neural target, and the frequency may be selected for a given application to be high enough (e.g. 200 Hz) to quickly deplete the presynaptic terminal of its ability to communicate across the synaptic cleft to provide an effective depletion block for that application.

Some embodiments may ramp up stimulation. Ramping up the stimulation may provide a graded block that may make the stimulation more tolerable. In a neural muscular junction depletion block, for example, the ramped stimulation may reduce the force of the one initial muscle activity at start of stimulation by creating an initial period of graded block. Some embodiments may change the frequency of stimulation signal during the block. Thus, higher frequency stimulations may be used to quickly obtain the block, and then lower frequency stimulation may be used to maintain the block that was previously obtained. For example, an initial frequency (e.g. 260 Hz) may be used to quickly achieve depletion block followed by a second frequency (e.g. 130 Hz) to maintain the depletion block. The frequency of stimulation is related to how long for complete or 90% depletion block. For example, frequencies less than about 100 Hz provide tetanic contraction. Frequencies within the range of about 100 to about 150 Hz provide a 90% depletion block in about 10 to 4 seconds. Frequencies within the range of about 200 to 1000 Hz provides a 90% depletion block less than one second (e.g. on the order of milliseconds). Frequencies greater than 1000 Hz start to enter into nerve conduction block.

Figure 7:
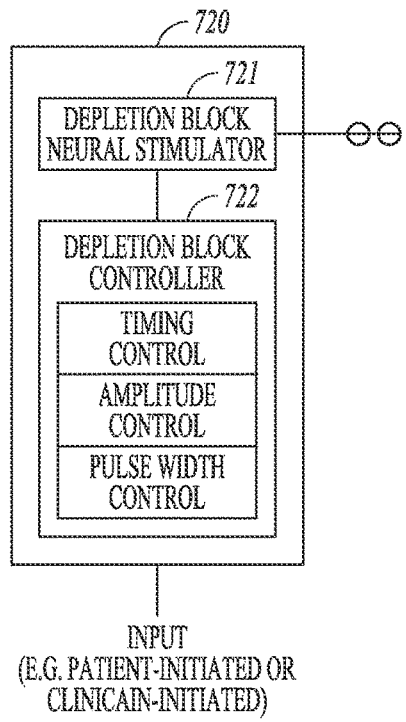
FIG. 7 illustrates, by way of example and not limitation, an embodiment of a system for delivering depletion block stimulation.

FIG. 7 illustrates, by way of example and not limitation, an embodiment of a system for delivering depletion block stimulation. The illustrated system includes a depletion block neural stimulator 721 operably connected to a depletion block controller 722. The depletion block neural stimulator may be configured to deliver a current to a neural target using electrode(s) operationally positioned proximate to the neural target. The electrodes may be configured in a unipolar stimulation arrangement, or may be configured in a bipolar stimulation arrangement as generally illustrated by the electrodes on the stimulation lead. The depletion block neural stimulator 721 is configured to deliver stimulation with a frequency that is between 100 Hz and 1 kHz. As identified above, this frequency ranges depletes the ability of the presynaptic terminal to communicate across the synaptic cleft to the postsynaptic membrane. The depletion block controller 722 may be configured to control the timing of the depletion stimulation from the depletion block neural stimulator. For example, the depletion block controller may be configured to control the initiation of the depletion block, or control the end of the depletion block, or control both the initiation and the termination of the depletion block. The controller may receive an input, such as a patient-initiated input and/or a clinician initiated input, and the timing of the depletion block may be based on this input. Where the system includes an implantable device configured to deliver the depletion block, the patient-initiated input may be a magnet or other communication device configured to communicate with the implantable medical device. Thus, the patient may initiate the depletion block in response to a perceived physiological condition that is indicated for the depletion block. By way of example and not limitation, the patient may initiate the block to treat a migraine headache or other pain. In another example, a clinician may trigger to block to perform a surgical procedure. Some embodiments may automatically receive inputs from the system, such as sensor inputs or interrupts that may identify a condition of a patient or of a therapy that is being delivered to the patient. For example, the system may receive a signal from another device. One such example is a defibrillator, which may send a signal to trigger a depletion block to control discomfort in preparation for the defibrillation shock. The illustrated controller may also control an amplitude of the depletion block signal and/or a pulse width of the depletion block signal to cause the depletion block signal to capture the desired nerve fibers within the targeted nerve.

Figure 8:
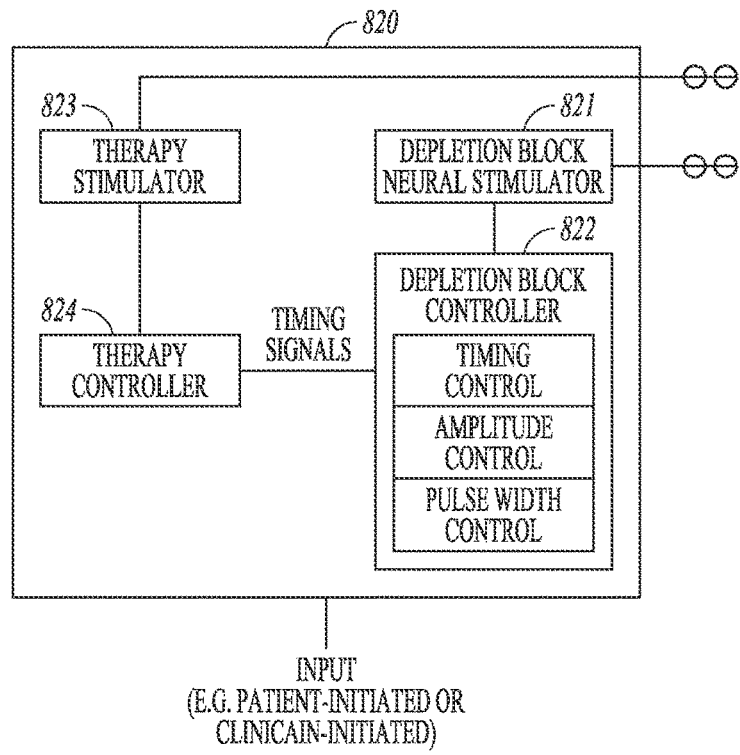
FIG. 8 illustrates, by way of example and not limitation, an embodiment of a system for delivering depletion block stimulation and delivering a therapy.

FIG. 8 illustrates, by way of example and not limitation, an embodiment of a system for delivering depletion block stimulation and delivering a therapy. Examples of such therapy may include various neural stimulation therapies or myocardial therapies. The illustrated system 820 has similarities to system 720 in FIG. 7, and includes, in addition to the depletion block neural stimulator 820 and depletion block controller 821, a therapy stimulator operably connected to a therapy controller configured to control the delivery of the therapy. The therapy controller 824 and depletion block controller 822 may communicate to provide timing signals, for example, or other information useful to coordinate the therapy and the depletion block. The therapy stimulation may be delivered using one set of electrodes and the depletion block stimulation may be delivered using another set of electrodes, such that the neural target for the therapy is different from the neural target for the depletion block. The therapy stimulation and depletion block stimulation may share at least one electrode. The therapy stimulation and depletion block stimulation may share all electrodes such that the neural target for therapy is the neural target for the depletion block.

Figure 9:
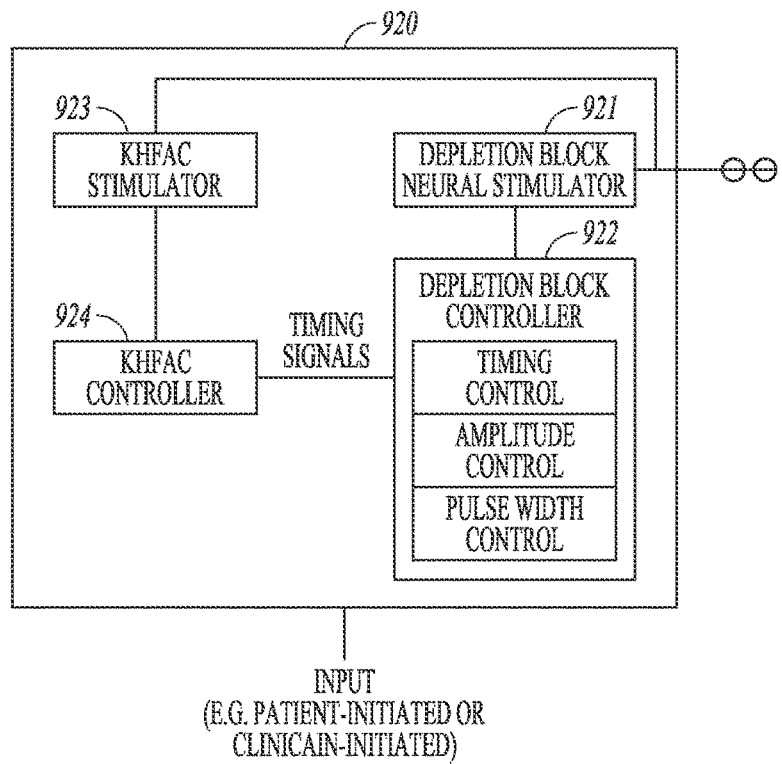
FIG. 9 illustrates, by way of example and not limitation, an embodiment of a system for delivering depletion block stimulation in conjunction with a kilo high frequency AC nerve block.

FIG. 9 illustrates, by way of example and not limitation, an embodiment of a system for delivering depletion block stimulation in conjunction with a kilo high frequency AC nerve block. The illustrated system 920 has similarities to system 820 in FIG. 8 including the depletion block neural stimulator 921 and the depletion block controller 922. In the embodiment illustrated in FIG. 9, the therapy stimulator includes a KHFAC stimulator configured to provide a nerve block that blocks action potentials from being propagated in the nerve, and the therapy controller includes an KHFAC controller configured to control the KHFAC stimulator. The therapy controller 924 and depletion block controller 922 may communicate to provide timing signals, for example, or other information useful to coordinate the therapy and the depletion block. Such timing signals may be used to deliver a depletion block to alleviate unpleasant sensations at the beginning of KHFAC stimulation. The depletion block signal also has an onset response, but the onset response for the depletion block signal is short and less detrimental than the onset for the KHFAC block and the depletion block onset response may be mitigated using techniques such as ramping the amplitude, for example.

Figure 10:
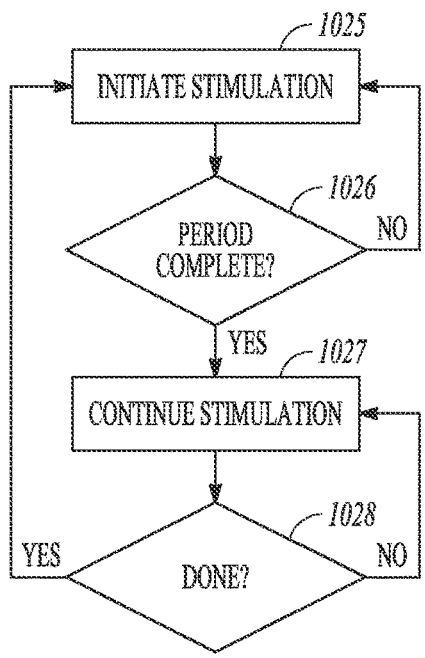
FIG. 10 illustrates, by way of example and not limitation, an embodiment of a process for delivering a presynaptic terminal depletion block.

FIG. 10 illustrates, by way of example and not limitation, an embodiment of a process for delivering a presynaptic terminal depletion block. At 1025 the depletion block stimulation is initiated. The patient may initiate the depletion block stimulation. A clinician may initiate the depletion block stimulation. The depletion block stimulation may be automatically initiated in response to a detected event or sensor input, or in response to a communicated signal from another system, or in response to a programmed therapy schedule. Once initiated, the stimulation may continue until the stimulation period is complete. Some embodiments may allow for the patient or clinician to override the stimulation before the period is complete, or for the system to override the stimulation before the period is complete. If the stimulation period is complete at 1026, the process returns to 1025 to wait for the next command to initiate stimulation. If the stimulation is not complete at 01126, the process proceeds to 1027 to continue stimulation. If the stimulation is not complete at 1028, the process returns to 1027.

FIG. 11 illustrates, by way of example and not limitation, an embodiment of a process for titrating a presynaptic terminal depletion block. The depletion block stimulation is delivered at 1129. If the stimulation is tolerable to the patient as indicated at 1130, the process returns to 1129 to continue to deliver the depletion block stimulation. If the stimulation is not tolerable at 1130, the process proceeds to 1131 to temporarily halt the depletion block stimulation and to 1132 to titrate the therapy to make the therapy more tolerable. At 1133, it is determined if the stimulation is tolerable. If it is not tolerable, the process returns to 1132 to further titrate the stimulation. If the stimulation is tolerable, the process may enable or re-enable the stimulation feature at 1134 to allow the depletion block stimulation to be delivered at 1129. The titration protocol may be used the intensity of the stimulation to increase or decrease the number of axons captured by the stimulation. In some embodiments, the titration protocol provides a rest or "wash-out" period to allow restoration of the neurotransmitters before adjusting the intensity of the stimulation.

FIG. 12 illustrates, by way of example and not limitation, an embodiment of a process for validating a presynaptic terminal depletion block. Some system embodiments may be designed with a system validation feature that can be used to confirm capture by disabling the stimulation for a period of time. The disabling of the stimulation may be clinician-initiated or may be patient-initiated or may be automatic with patient disable capability, or may be a combination of two or more of clinician-initiated, patient-initiated, automatic with patient disable capability. Some embodiments may automatically re-enable after a time period expires to ensure best therapy delivery mode. At 1235, depletion block stimulation is delivered. If it is not time for a system check to valid therapy delivery at 1236, the process returns to 1235 to continue delivering the therapy. If it is time for a system check at 1236, the process proceeds to 1237 to temporarily halt stimulation 1237 to allow the system check to be performed at 1238. The patient may be able to sense that the beneficial effects of the depletion block has been stopped or reduced, which confirms that the stimulation is providing an effective depletion block. Sensors may be used to monitor the post-synaptic activity (e.g. laryngeal vibration when a neural stimulation therapy is being applied to the cervical vagus nerve and a depletion block is applied to provide a depletion block of the presynaptic terminals of the nerve fibers that innervate the laryngeal muscle), and sense a change in the post-synaptic activity between a time when the depletion block is being delivered and a time when the depletion block is not be delivered. Once the system check is completed at 1239, the process may return to delivering the depletion block stimulation at 1235.

The depletion block may be used alone, or in conjunction with another blocking technique or another stimulation therapy. An application, by way of example and not limitation, may apply the depletion block to provide pain relief in patients. For example, a depletion block may be implemented on an appropriate nerve to reduce or avoid lower back pain, phantom limb pain or headaches. The depletion block is much more energy-efficient than kilohertz high frequency AC (KHFAC) blocks. Depending on the specific parameters of the depletion block stimulation and the KHFAC block, the depletion block stimulation may be more efficient by a factor of about 100. Some embodiments for controlling pain may be provided in conjunction with an applied therapy that may cause pain. By way of example and not limitation, some embodiments provide depletion block capabilities with a cardioverter/defibrillator. The system may be a single device or multiple devices. The system is configured to provide the depletion block in preparation for and during a therapeutic shock applied across the heart by the cardioverter/defibrillator, thus eliminating or reducing pain associated with the shock. Some embodiments may be configured to treat migraines or other pain.

In an example the depletion block may be implemented with a high frequency nerve block to avoid the pain associated with the high frequency nerve block. KHFAC can block nerve conduction in peripheral nerves. However KHFAC produces an intense burst of firing in the nerve when first initiated, which may cause an uncomfortable sensation. This onset response can last from milliseconds to more than 30 seconds. The depletion block may be delivered with or just prior to delivery of the KHFAC block to produce a complete nerve block without the painful side effects induced by the onset response for KHFAC or without the safety issues incurred with DC block. In some embodiments the same pair of electrodes may be used to deliver the depletion block and the KHFAC block. In some embodiments the neurotransmitter depletion block may be delivered using bipolar electrodes and the KHFAC nerve block is unipolar back to the can. The depletion block electrodes may surround the KHFAC nerve block unipolar electrode.

FIG. 13 illustrates, by way of example and not limitation, an embodiment of a process for delivering a presynaptic terminal depletion block with a high frequency AC nerve block. The process waits for an initiation signal at 1340. In response to the initiation signal, the process proceeds to deliver the depletion block stimulation at 1341. The depletion block stimulation continues until the depletion block is achieved. When the depletion block is achieved at 1342 the process proceeds to 1343 to deliver KHFAC nerve block stimulation to block action potentials in the nerve. The depletion block may block the discomfort associated with the onset of the KHFAC. After the KHFAC is delivered and is blocking the action potentials, the depletion block may be stopped. The KHFAC continues to be delivered at 1343 until the KHFAC process is complete at 1344.

FIG. 14 illustrates, by way of example and not limitation, an embodiment of a process for ramping up a presynaptic terminal depletion block in preparation with a high frequency AC nerve block. The process illustrated in FIG. 14 is similar to the process illustrated in FIG. 13, except that the amplitude of the stimulation of the depletion block is ramped up to avoid tolerance of the depletion block. The process waits for an initiation signal at 1445. In response to the initiation signal, the process initiates a depletion block by ramping up an amplitude of a depletion block signal at 1446, and then proceeds to deliver the depletion block stimulation at 1447. The depletion block stimulation continues until the depletion block is achieved. When the depletion block is achieved at 1448 the process proceeds to 1449 to deliver KHFAC nerve block stimulation to block action potentials in the nerve. The depletion block may block the discomfort associated with the onset of the KHFAC. After the KHFAC is delivered and is blocking the action potentials, the depletion block may be stopped. The KHFAC continues to be delivered at 1449 until the KHFAC process is complete at 1450.

In an example, the depletion block may be used in various applications to provide a partial depletion block, which also may be referred to as a graded depletion block. The amplitude of the current may be reduced below the saturation threshold so that only some of the nerve fibers in the targeted region are captured, which determines a percentage of the presynaptic terminals that are depleted from their ability to communicate across the synaptic cleft when a depletion block frequency is applied. Graded depletion blocks may be used to reduce or remove system internal nerve activity such as spasticity. Clinically, spasticity is defined as velocity dependent resistance to stretch where a lack of inhibition results in excessive contraction of the muscles. For example, post-stroke patients may develop spasticity in arms or legs. A partial depletion block may allow the patient to gain some control of their arms or legs. A graded block may allow "natural" reflexes or muscle activity to still proceed while blocking over activity, or unwanted stimulation from another source. Graded blocks may also be used to reduce or remove the induced nerve activity that may be side effect of other stimulation (e.g. myocardial, muscular, or other nerve stimulation). Thus, the graded depletion block provides a reversible, on demand block that is enough to avoid side effects.

In an example the depletion block may be implemented to relieve spasmodic peripheral nerve pain. These episodes may occur a few times a day for periods of many minutes. The neurotransmitter block may be initiated by the patient, or may be automatically initiated using sensors. Various embodiments may implement techniques for directed propagation of nerve fiber stimulation such that block in one direction (block hyper excitability input that is causing spasticity). The nerve may be stimulated in the other direction to provide muscle control.

Figure 15:
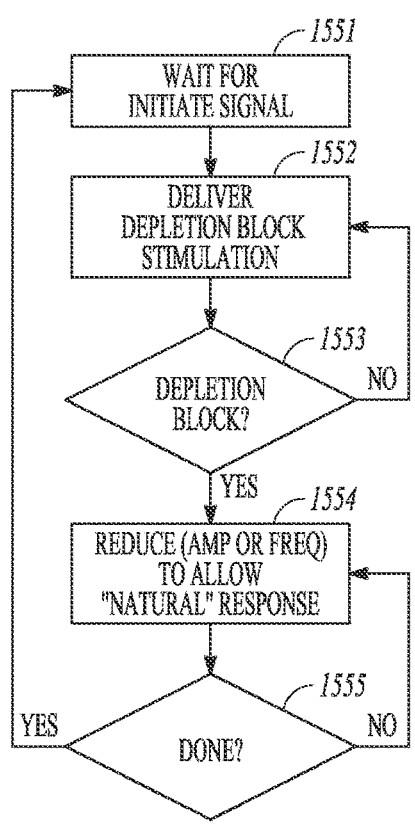
FIG. 15 illustrates, by way of example and not limitation, an embodiment of a process for delivering a presynaptic terminal depletion block and then reducing the block to reduce the number of axons blocked to allow a more natural neural response.

FIG. 15 illustrates, by way of example and not limitation, an embodiment of a process for delivering a presynaptic terminal depletion block and then reducing the block to reduce the number of axons blocked to allow a more natural neural response. At 1515, the process waits for an initiation signal. Upon receipt of the initiation signal, the process delivers depletion block stimulation at 1552 until a depletion block is achieved at 1553. After the depletion is achieved, the amplitude or frequency of the depletion block signal may be reduced at 1554 which may be desired to promote a more natural response. The process may continue at the reduced depletion block stimulation until the process is terminated at 1555.

Figure 16:
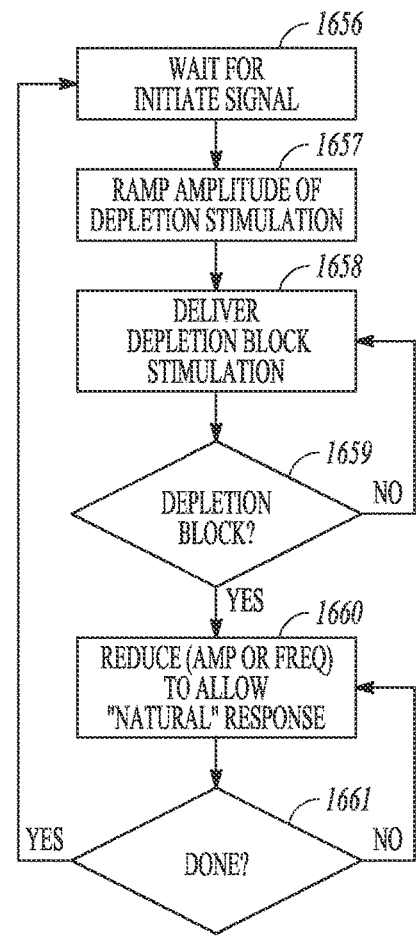
FIG. 16 illustrates, by way of example and not limitation, an embodiment of a process for ramping up a presynaptic terminal depletion block and then reducing the block to reduce the number of axons blocked to allow a more natural neural response.

FIG. 16 illustrates, by way of example and not limitation, an embodiment of a process for ramping up a presynaptic terminal depletion block and then reducing the block to reduce the number of axons blocked to allow a more natural neural response. The process illustrated in FIG. 16 is similar to the process illustrated in FIG. 15, except that the process further ramps up the amplitude of the depletion block stimulation which may be beneficial to improve tolerance to the depletion block. At 1656, the process waits for an initiation signal. Upon receipt of the initiation signal, the process initiates a depletion block by ramping up an amplitude of a depletion block signal, and then delivers the depletion block stimulation at 1658 until a depletion block is achieved at 1659. After the depletion is achieved, the amplitude or frequency of the depletion block signal may be reduced at 1660 which may be desired to promote a more natural response. The process may continue at the reduced depletion block stimulation until the process is terminated at 1661.

In an example the neurotransmitter block may be implemented to reduce the pain or applied anesthesia during a medical procedures such as a surgical procedure or an ablation procedure. By way of example renal nerve ablation for hypertension therapy currently involves the use of general anesthesia. However, it is believed that the neurotransmitter block as described herein, which seizes neurotransmitter communication in about 0.1 seconds of the block stimulation is initiated, may be effective to reduce pain that thus eliminate the need for general anesthesia during a renal nerve ablation procedure. The neurotransmitter block can be used to stop communication on nerve fibers to muscles as well as from sensory organs (e.g. pain) to the spinal cord and brain.

The replacement of general anesthesia with a depletion nerve block can allow the ablation procedure to be performed very quickly. The ablation procedure may include: inserting and positioning of ablation catheter in the renal artery and inflation of balloon; contacting verification via impedance measurement, initiation of proximal nerve block; ablation; and catheter extraction. In some embodiments, the system may be used to provide the physician with a feedback of success using a comparison of proximal electrode stimulation prior to and following ablation. This proximal stimulation before and after the ablation can be used to verify that enough nerves have been ablated. The entire procedure may be accomplished in about 20 minutes. Most of this time is used to insert the catheter at the beginning of the procedure (e.g. about 15 minutes) and to extract the catheter at the end of the procedure (e.g. about 5 minutes). The proximal nerve block only adds a short time on the order of a second or so to the procedure. Additionally, the neurotransmitter block is quickly reversed on the order of 1 second after the ablation.

Certain physiological areas to be ablated that can quickly show an observable response to the therapy. A depletion block may be applied to test a targeted region before ablation to determine if the ablation therapy to the targeted region would be successful. Thus, the ablation location may be verified before ablation. This pre-ablation testing is likely to increase chances of successful ablation. Further, the system may be used after ablation but before catheter extraction to determine if enough neural tissue was ablated. In addition to renal denervation, other examples of ablation procedures include carotid body denervation and atrial fibrillation ablation.

Figure 17:
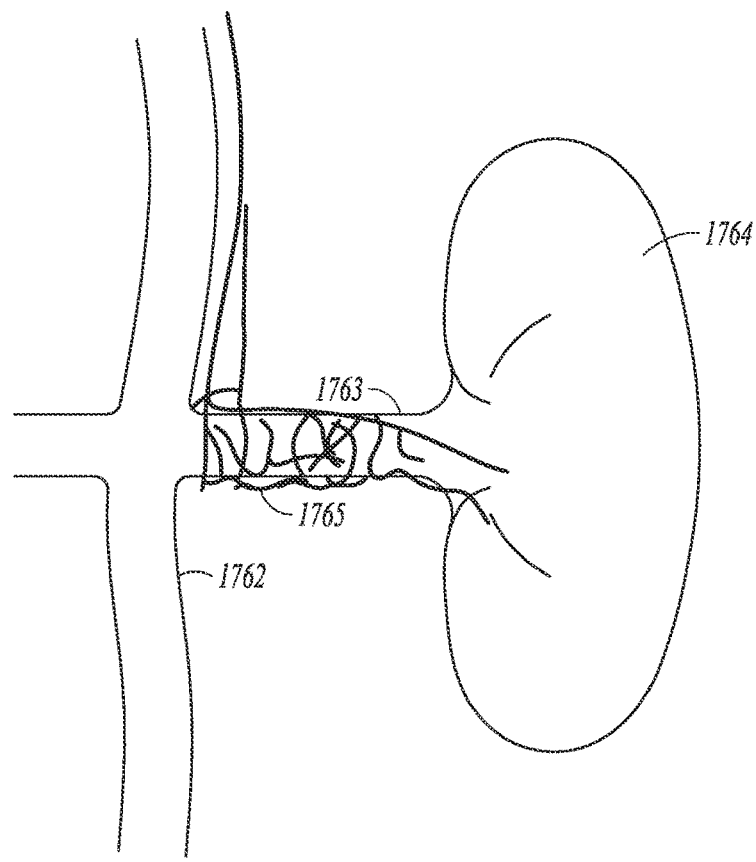
FIG. 17 generally illustrates physiology of the kidney and renal nerve.
Figure 18:
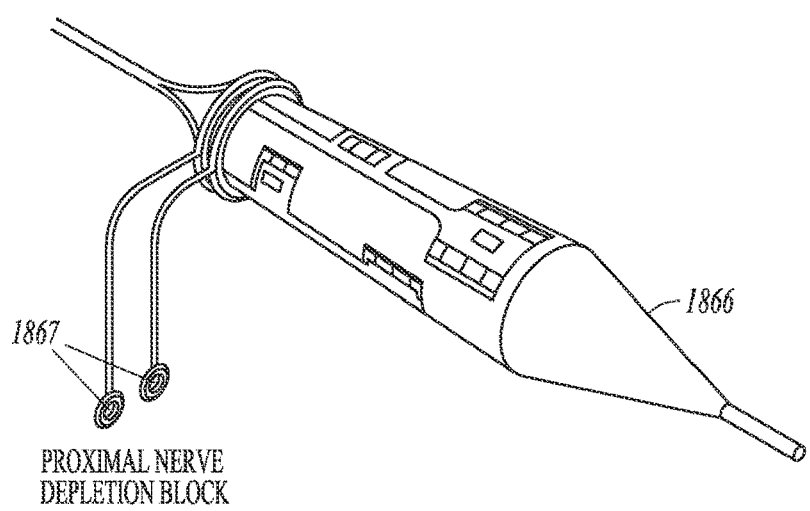
FIG. 18 illustrates, by way of example and not limitation, an ablation catheter with proximal depletion block electrodes such as may be used to provide a depletion block to alleviate the pain associated with the ablation procedure.

FIG. 17 generally illustrates physiology of the kidney and renal nerve. Blood flows from the aorta 1762 through a renal artery 1763 to a kidney 1764. A renal nerve descends and branches out into a complex pattern of neural fibers 1765 that course along the renal artery to the kidney. Renal nerve denervation has been suggested as a method for treating hypertension. The systemic blood pressure of the patient can be reduced by ablating some of these nerves. Renal nerve ablation may involve inserting a catheter up through the aorta into the renal artery, and deliver radiofrequency energy to ablate some of the neural tissue. Depletion block electrodes may incorporated in the ablation catheter to deliver depletion block stimulation to a neural target. The depletion block electrodes may be positioned on the ablation catheter to target a desired nerve to block pain during the procedure. FIG. 18 illustrates, by way of example and not limitation, an ablation catheter 1866 with proximal depletion block electrodes 1867 such as may be used to provide a depletion block to alleviate the pain associated with the ablation procedure. The depletion block electrodes may be positioned on the ablation catheter near a target where the ablation is to be performed for use in providing a quick depletion block to confirm the target for ablation. For example, one can figure out if the electrodes are in the desirable spot by stimulating near the kidney and monitoring for an acute change in bio-potentials such as heart rate, blood pressure, etc. One can then block proximally and stimulate distally to see if the acute change persists, and then can block proximally and heat or otherwise destroy nerve tissue distally.

Other anatomical regions innervated by neural tissue in a complex manner include epicardial ganglionated plexi (GP). GP are organized nerves present in cardiac fat pads on the epicardial surface of the heart and the ligament of Marshall, which is located between the left atrial appendage and the left pulmonary veins and is believed to be a source of AF. The GPs are part of an epicardial neural network that comprises multiple ganglia with interconnecting neurons and axons, including afferent sensory fibers and sympathetic and parasympathetic efferents.

For example, ablation of GP is a potential target for the treatment of AF. Endocardial RF GP ablation however leads to injury to intervening atrial myocardium, so unnecessary ablation of innocent tissue should be avoided. A discussion of GP ablation for atrial fibrillation may be found in Yong Zhang, Mei Gao, Jiangrong Wang and Yinglong Hou (2012). Ganglionated Plexi Ablation for Atrial Fibrillation, Atrial Fibrillation—Basic Research and Clinical Applications, Prof. Jong-Il Choi (Ed.), ISBN: 978-953-307-399-6, InTech, Available from: http://www.intechopen.com/books/atrial-fibrillation-basic-rsearch-andclinical-applications/ganglionated-plexi-ablation-for-atrial-fibrillation, which is incorporated herein by reference in its entirety. This reference indicates that GPs include the anterior right GP (ARGP) at the right superior PV (RSPV)—atrial junction, the inferior right GP (IRGP) at the junction of inferior vein cava and both atria; the superior left GP (SLGP) near the left superior PV (LSPV)—atrial junction and left pulmonary artery, and inferior left GP (ILGP) at the left inferior PV (LIPV)—atrial junction.

Some embodiments may be used to depleting the nerves to the legs' arteries and veins' muscles, such as may be performed using a catheter approach. This may be used to treat hypertension by relaxing the muscles in the legs and providing a quick reduction in blood pressure. Rather than block, some embodiments may stimulate these muscles to treat hypotension or to "pump" blood from legs. This may provide more cardiac pre-load and function like a cardiac assist device. A combination of stimulation and block may be used to pump blood up better or relax the muscles around/near the arteries/veins more and hence get better flow Some electrodes may have surfaces that are relatively smooth. Some electrodes may have protrusions that penetrate some distance into the vessel wall for improved proximity to the nerve and/or improved 'fixation' in the vessel. Some electrodes may have a non-penetrating surface texture that may improve fixation. The protrusions may be "spikes" or "bumps". The protrusions may be configured to provide a more definite surface connection, and may offer more neural selectivity. For example, spikes pierce into the vessel wall and get the electrode tips closer to the neural targets. Thus, the protrusions may both bring the electrodes into closer proximity to the nerves and improve the anchoring of the electrode by penetrating through some or all of the vessel wall. These protrusions (e.g. spikes) may engage the surface after the device is expanded. The expandable device may be similar to a stent. The protrusions may be on a ring, and pushed outward into engagement with the vessel wall by an inflatable device (e.g. balloon) during the implantation procedure.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
 a depletion block neural stimulator configured to deliver a depletion block stimulation to a nerve; and
 a depletion block controller configured to communicate with the depletion block neural stimulator and control the depletion block stimulation to provide a series of pulses at a pulse frequency within a range between 100 Hz to 700 Hz, the series of pulses including an amplitude and a pulse width to depolarize the nerve such that the depletion block stimulation induces action potentials in the nerve and depletes neurotransmitters to prevent action potentials from being communicated across a synaptic cleft, the depletion block controller configured to receive a start depletion block signal and respond to the received start depletion block signal by initiating the delivery of the depletion block stimulation to the nerve, and the depletion block controller configured to receive a stop depletion block signal and respond to the received stop depletion block signal by terminating the delivery of the depletion block stimulation to the nerve, wherein the depletion block controller is configured to change the pulse frequency of the depletion block stimulation, and is further configured to initiate the depletion block stimulation with a first pulse frequency and maintain the depletion block stimulation with a second pulse frequency less than the first pulse frequency.

2. The system of claim 1, further comprising:
an electrical therapy stimulator configured to generate and apply electrical stimulation to a patient; and
a therapy controller configured to communicate with the electrical therapy stimulator and control the electrical stimulation, the therapy controller configured to send the start depletion block signal and the stop depletion block signal, and further configured to control the electrical therapy stimulator to generate and apply the electrical stimulation during a time period between sending the start and stop depletion block signals.

3. The system of claim 2, wherein the electrical therapy stimulator includes an ablation system configured to ablate tissue using the electrical stimulation during an ablation procedure, and the depletion block neural stimulator is configured to reduce pain during the ablation procedure.

4. The system of claim 2, wherein the electrical therapy stimulator includes a kilohertz high frequency alternating current (KHFAC) nerve block stimulator configured to deliver an KHFAC nerve block stimulation to the nerve, the nerve block stimulation including a series of pulses at a pulse frequency over 1 kHz to arrest action potentials in the axon; and the therapy controller is configured to send the start and stop depletion block signals near the beginning of the KHFAC nerve block stimulation to alleviate an onset response for the KHFAC nerve block stimulation.

5. The system of claim 1, wherein the depletion block stimulator is configured to deliver the depletion block stimulation to the nerve selected to relieve spasmodic peripheral nerve pain, the system further comprising a patient input configured to receive a patient-initiatedsignal, the depletion block controller configured to send the start depletion block signal in response to receiving the patient-initiated signal.

6. The system of claim 1, wherein the depletion block stimulator is configured to deliver the depletion block stimulation to the nerve selected to relieve spasmodic peripheral nerve pain, the system further comprising a muscle spasm detector configured to detect a spasmodic episode, the depletion block controller configured to send the start depletion block signal in response to detecting a spasmodic episode.

7. The system of claim 1, wherein the depletion block stimulator is configured to deliver the depletion block stimulation to the nerve selected to relieve spasmodic peripheral nerve pain, the depletion block controller configured to adjust at least one of the amplitude or the pulse width of the depletion block stimulation to control a graded depletion block to allow some neurotransmitters to be released from the presynaptic terminal into the extracellular space.

8. The system of claim 1, wherein the depletion block controller is configured to implement a process to automatically transition through at least two frequency stages, wherein a first pulse frequency stage includes the first pulse frequency and a second pulse frequency stage includes the second pulse frequency, and the first pulse frequency stage has a duration corresponding to a time period such that the depletion block controller transitions from the first pulse frequency stage to the second pulse frequency stage after the time period.

* * * * *